(12) United States Patent
Dar et al.

(10) Patent No.: US 8,868,217 B2
(45) Date of Patent: Oct. 21, 2014

(54) ELECTRODE FOR MUSCLE STIMULATION

(75) Inventors: Amit Dar, Kfar Hess (IL); Mark Rubin, Moshav Nitzanai Oz (IL); Shmuel Springer, Modi'in (IL); Amir Cohen, Ra'anana (IL)

(73) Assignee: Bioness Neuromodulation Ltd., Raanana (IL)

( * ) Notice: Subject to any disclaimer, the term of this patent is extended or adjusted under 35 U.S.C. 154(b) by 122 days.

(21) Appl. No.: 13/169,553

(22) Filed: Jun. 27, 2011

(65) Prior Publication Data

US 2012/0330394 A1     Dec. 27, 2012

(51) Int. Cl.
     *A61N 1/04*        (2006.01)
     *A61F 5/01*        (2006.01)

(52) U.S. Cl.
     CPC ............ *A61N 1/0452* (2013.01); *A61F 5/0102* (2013.01); *A61N 1/0456* (2013.01); *A61N 1/0484* (2013.01)
     USPC .................... 607/152; 607/1; 607/2; 607/115; 607/149; 600/372; 600/382; 600/383; 600/384; 600/386; 600/388; 600/389; 600/390; 600/391; 600/392; 600/393

(58) Field of Classification Search
     USPC ................. 600/372, 382–384, 386, 388–393; 607/1–2, 115, 149, 152
     See application file for complete search history.

(56) References Cited

U.S. PATENT DOCUMENTS

| | | | |
|---|---|---|---|
| 1,422,396 A | 7/1922 | Wappler | |
| 1,644,803 A | 10/1927 | Wappler | |
| 3,204,637 A | 9/1965 | Frank et al. | |
| 3,344,792 A | 10/1967 | Offner et al. | |
| 3,881,496 A | 5/1975 | Vredenbregt et al. | |
| 4,381,012 A | 4/1983 | Russek | |
| 4,432,368 A | 2/1984 | Russek | |
| 4,558,704 A | 12/1985 | Petrofsky | |
| 4,580,569 A | 4/1986 | Petrofsky | |
| 4,586,495 A | 5/1986 | Petrofsky | |
| 4,697,808 A | 10/1987 | Larson et al. | |

(Continued)

FOREIGN PATENT DOCUMENTS

| | | |
|---|---|---|
| JP | S60-119949 | 6/1985 |
| JP | 2004-313555 A | 11/2004 |
| WO | WO 2004/098703 | 11/2004 |
| WO | WO 2006/113801 | 10/2006 |

OTHER PUBLICATIONS

Office Action for U.S. Appl. No. 13/022,149, mailed Jan. 15, 2013.

(Continued)

*Primary Examiner* — Deborah Malamud
(74) *Attorney, Agent, or Firm* — Cooley LLP

(57) ABSTRACT

Devices and methods of treating a targeted body tissue by stimulating the body tissue with an electric current. In one embodiment, an apparatus includes an electrode carrier configured to be removably coupled to an interior surface of an orthosis. The electrode carrier includes a recess configured to matingly receive a portion of an electrode. The electrode carrier is electrically coupled to the electrode when the portion of the electrode is disposed within the recess. A connection member is electrically coupled to the electrode carrier and is configured to be releasably coupled to a surface of the orthosis. The electrode carrier is electrically coupled to the orthosis when the connection member is coupled to the orthosis. In some embodiments, the electrode carrier is configured to be removably coupled to the interior surface of the orthosis. In some embodiments, at least a portion of the electrode is constructed of an absorptive material.

17 Claims, 34 Drawing Sheets

(56) References Cited

U.S. PATENT DOCUMENTS

| | | |
|---|---|---|
| 4,777,954 A | 10/1988 | Keusch et al. |
| 4,832,033 A | 5/1989 | Maher et al. |
| 4,982,732 A | 1/1991 | Morris |
| 5,112,296 A | 5/1992 | Beard et al. |
| 5,121,747 A | 6/1992 | Andrews |
| 5,167,229 A | 12/1992 | Peckham et al. |
| 5,277,697 A | 1/1994 | France et al. |
| 5,285,781 A | 2/1994 | Brodard |
| 5,330,516 A | 7/1994 | Nathan |
| 5,437,619 A | 8/1995 | Malewicz et al. |
| 5,476,441 A | 12/1995 | Durfee et al. |
| 5,487,759 A | 1/1996 | Bastyr et al. |
| 5,540,735 A | 7/1996 | Wingrove |
| 5,562,707 A | 10/1996 | Prochazka et al. |
| 5,628,722 A | 5/1997 | Solomonow et al. |
| 5,643,332 A | 7/1997 | Stein |
| 5,724,996 A | 3/1998 | Piunti |
| 5,748,845 A | 5/1998 | Labun et al. |
| 5,814,093 A | 9/1998 | Stein |
| 5,851,191 A | 12/1998 | Gozani |
| 5,861,017 A | 1/1999 | Smith et al. |
| 5,916,159 A | 6/1999 | Kelly et al. |
| 5,951,598 A | 9/1999 | Bishay et al. |
| 5,983,140 A | 11/1999 | Smith et al. |
| 6,002,965 A | 12/1999 | Katz et al. |
| 6,019,877 A | 2/2000 | Dupelle et al. |
| 6,064,912 A | 5/2000 | Kenney |
| 6,129,695 A | 10/2000 | Peters et al. |
| 6,282,448 B1 | 8/2001 | Katz et al. |
| 6,308,102 B1 | 10/2001 | Sieracki et al. |
| 6,438,428 B1 | 8/2002 | Axelgaard et al. |
| 6,445,955 B1 | 9/2002 | Michelson et al. |
| 6,456,884 B1 | 9/2002 | Kenney |
| 6,456,885 B1 | 9/2002 | Shiba et al. |
| 6,496,739 B2 | 12/2002 | Arbel |
| 6,507,757 B1 | 1/2003 | Swain et al. |
| 6,564,103 B2 | 5/2003 | Fischer et al. |
| 6,567,706 B2 | 5/2003 | Bar-Or et al. |
| 6,571,115 B2 | 5/2003 | Axelgaard et al. |
| 6,607,500 B2 | 8/2003 | Da Silva et al. |
| 6,618,624 B2 | 9/2003 | Elias |
| 6,829,510 B2 | 12/2004 | Nathan et al. |
| 7,011,637 B2 | 3/2006 | Sherman et al. |
| 7,146,220 B2 | 12/2006 | Dar et al. |
| 7,158,822 B2 | 1/2007 | Payne, Jr. |
| 7,162,305 B2 | 1/2007 | Tong et al. |
| 7,337,007 B2 | 2/2008 | Nathan et al. |
| 7,403,821 B2 | 7/2008 | Haugland et al. |
| 7,410,471 B1 | 8/2008 | Campbell et al. |
| 7,416,537 B1 | 8/2008 | Stark et al. |
| 7,756,585 B2 | 7/2010 | Embrey et al. |
| 7,785,279 B2 | 8/2010 | Sankai |
| 7,899,556 B2 | 3/2011 | Nathan et al. |
| 8,070,703 B2 | 12/2011 | Skahan et al. |
| 8,209,022 B2 | 6/2012 | Dar et al. |
| 8,209,036 B2 | 6/2012 | Nathan et al. |
| 2001/0039444 A1 | 11/2001 | Bar-Or et al. |
| 2002/0077688 A1 | 6/2002 | Kirkland |
| 2003/0040788 A1 | 2/2003 | Dupelle et al. |
| 2003/0050673 A1 | 3/2003 | Yamazaki et al. |
| 2003/0065368 A1 | 4/2003 | Van Der Hoeven |
| 2003/0083596 A1 | 5/2003 | Kramer et al. |
| 2003/0114892 A1 | 6/2003 | Nathan et al. |
| 2003/0114894 A1 | 6/2003 | Dar et al. |
| 2004/0082979 A1 | 4/2004 | Tong et al. |
| 2004/0122483 A1 | 6/2004 | Nathan et al. |
| 2004/0172097 A1 | 9/2004 | Brodard et al. |
| 2004/0173220 A1 | 9/2004 | Harry et al. |
| 2004/0243197 A1 | 12/2004 | Demian |
| 2004/0254624 A1 | 12/2004 | Johnson |
| 2005/0043660 A1 | 2/2005 | Stark et al. |
| 2005/0085706 A1 | 4/2005 | Perrault et al. |
| 2006/0211956 A1 | 9/2006 | Sankai |
| 2007/0106343 A1 | 5/2007 | Monogue et al. |
| 2007/0112394 A1 | 5/2007 | Nathan et al. |
| 2007/0179560 A1 | 8/2007 | Tong et al. |
| 2007/0197946 A1 | 8/2007 | Gilmour |
| 2007/0203533 A1 | 8/2007 | Goren et al. |
| 2008/0045872 A1 | 2/2008 | Bauerfeind et al. |
| 2008/0154113 A1 | 6/2008 | Zilberman |
| 2008/0154335 A1 | 6/2008 | Thrope et al. |
| 2008/0294080 A1 | 11/2008 | Adarraga |
| 2009/0012436 A1 | 1/2009 | Lanfermann et al. |
| 2009/0177131 A1 | 7/2009 | Dar et al. |
| 2011/0137375 A1 | 6/2011 | McBride |
| 2012/0203156 A1 | 8/2012 | Dar et al. |
| 2012/0330375 A1 | 12/2012 | Nathan et al. |
| 2012/0330395 A1 | 12/2012 | Dar et al. |

OTHER PUBLICATIONS

Examination Report for Australian Application No. 2006314072, mailed on May 5, 2010, 4 pages.

Examination Report for Australian Application No. 2006314072, mailed on Jul. 5, 2011, 2 pages.

Office Action for Canadian Application No. 2,632,196, mailed on Mar. 16, 2010, 4 pages.

Office Action for U.S. Appl. No. 11/380,430, mailed Nov. 13, 2009, 8 pages.

Office Action for U.S. Appl. No. 11/380,430, mailed Mar. 24, 2010, 12 pages.

Office Action for U.S. Appl. No. 11/380,430, mailed Sep. 1, 2010, 11 pages.

Popovic, et al., "Functional Electrical Stimulation for Grasping and Walking: Indications and Limitations," Spinal Cord, Jun. 2001, 22 pages.

Office Action for U.S. Appl. No. 12/096,077, mailed Apr. 5, 2012, 10 pages.

Office Action for U.S. Appl. No. 13/036,256, mailed Apr. 5, 2012, 8 pages.

International Search Report and Written Opinion for International Application No. PCT/IL2012/000063, mailed Jun. 29, 2012, 11 pages.

International Search Report and Written Opinion for PCT/IL2012/000260, mailed on Oct. 9, 2012, 13 pages.

Office Action for U.S. Appl. No. 13/532,597, mailed Apr. 23, 2013.

Offic'e Action for U.S. Appl. No. 13/022,149, mailed Jul. 15, 2013.

Supplementary European Search Report for European Application No. 06821561.5, mailed Dec. 16, 2013.

Office Action for Canadian Application No. 2,794,533, mailed Nov. 29, 2013.

Office Action for U.S. Appl. No. 13/532,603, mailed Nov. 29, 2013.

Office Action for Canadian Application No. 2,649,663, mailed Nov. 20, 2013.

Office Action for U.S. Appl. No. 12/299,043, mailed Jul. 5, 2013.

European Search Report for European Application No. EP 12197261.6, mailed Mar. 28, 2013.

Office Action for U.S. Appl. No. 13/022,149, mailed Feb. 6, 2014.

Alon, G. et al., "Persons with C5 or C6 tetraplegia achieve selected functional gains using a neuroprosthesis," Arch. Phys. Med. Rehabil., 84:119-124 (Jan. 2003).

"Clinical evaluation of the Ijubljana functional electrical peroneal brace," Subcommittee on Evaluation, Committee on Prosthetics Research and Development Division of Medical Sciences—National Research Council, National Academy of Sciences, Washington, D.C., Report E-7 (1973).

Daly, W. K., "Electrodes installed in roll-on suspension sleeves," From "MEC '02 The Next Generation," Proceedings of the 2002 MyoElectric Controls/Powered Prosthetics Symposium, Fredericton, New Brunswick, Canada: Aug. 21-23, 2002, University of New Brunswick, 3 pages.

Davis, R. et al., "Evaluation of electrical stimulation as a treatment for the reduction of spasticity," Bulletin of Prosthetics Research, Department of Medicine and Surgery Veterans Administration, Washington, D.C., pp. 302-309 (1974).

Duncan, R. M., "Basic principles of splinting the hand," Journal of the American Physical Therapy Association, 69(12):1104-1116 (1989).

(56) References Cited

OTHER PUBLICATIONS

Hart, R. L. et al., "A comparison between control methods for implanted FES hand-grasp systems," IEEE Transactions on Rehabilitation Engineering, 6(2):208-218 (Jun. 1998).

Hendricks, H. T. et al., "Functional electrical stimulation by means of the 'Ness Handmaster Orthosis' in chronic stroke patients: an exploratory study," Clinical Rehabilitation, 15:217-220 (2001).

Kralj, A. et al., "Functional electrical stimulation of the extremities: part 1," Journal of Medical Engineering and Technology, pp. 12-15 (Jan. 1977).

Kralj, A. et al., "Functional electrical stimulation of the extremities: part 2," Journal of Medical Engineering and Technology, pp. 75-80 (Mar. 1977).

Liberson, W. T. et al., "Functional Electrotherapy: Stimulation of the Peroneal Nerve Synchronized with the Swing Phase of the Gait of Hemiplegic Patients," Archives of Physical Medicine & Rehabilitation, pp. 101-105 (Feb. 1961).

Popovic, M. R. et al., "Neuroprostheses for grasping," Neurological Research, 24:443-452 (Jul. 2002).

Popovic, M. R. et al., "Functional electrical therapy: retraining grasping in spinal cord injury," Spinal Cord, 44:143-151 (2006).

Prochazka, A. et al., "The bionic glove: An electrical stimulator garment that provides controlled grasp and hand opening in quadriplegia," Arch. Phys. Med. Rehabil., 78:608-614 (Jun. 1997).

Stanic, U., "History of functional electrical stimulation," International Functional Electrical Stimulation Society, INS & IFESS Joint Congress, Sep. 16-20, 1998, Lucerne, Switzerland, 37 pages.

Stopar, M. et al., "New stimulators for cutaneous stimulation," Advances in External Control of Human Extremities, Proceedings of the Seventh International Symposium on External Control of Human Extremities, pp. 267-272 (1981).

Strojnik, P. et al., "Implantable stimulators for neuromuscular control," Chapter 78 in the Biomedical Engineering Handbook: Second Edition, Bronzino, J. D. (ed.), Boca Raton: CRC Press LLC (2000), 15 pages.

Uellendahl, J. E. et al., "Custom silicone sockets for myoelectric prostheses," Journal of Prosthetics and Orthotics, 18(2):35-40 (2006).

Uellendahl, J. E. et al., "Custom silicone sockets for myoelectric prostheses," From "MEC '05 Intergrating Prosthetics and Medicine," Proceedings of the 2005 MyoElectric Controls/Powered Prosthetics Symposium, held in Fredericton, New Brunswick, Canada, Aug. 17-19, 2005, 6 pages.

Vodovnik, L. et al., "Functional electrical stimulation for control of locomotor systems," CRC Critical Reviews in Bioengineering, 6(2):63-131 (Sep. 1981).

Ward, A. R. et al., "Russian electrical stimulation: The early experiments," Physical Therapy, 82(10):1019-1030 (Oct. 2002).

Waters, R. L. et al., "Effectiveness of selected surface electrodes for motor stimulation," Advances in External Control of Human Extremities, Proceedings of the Sixth International Symposium on External Control of Human Extremities, pp. 31-38 (1978).

Waters, R. et al., "Treatment of the hemiplegic upper extremity using electrical stimulation and biofeedback training," Report to the Veterans Administration, Contract V600P-1064-79, Funding Period Sep. 27, 1979-Sep. 30, 1980, pp. 251-266.

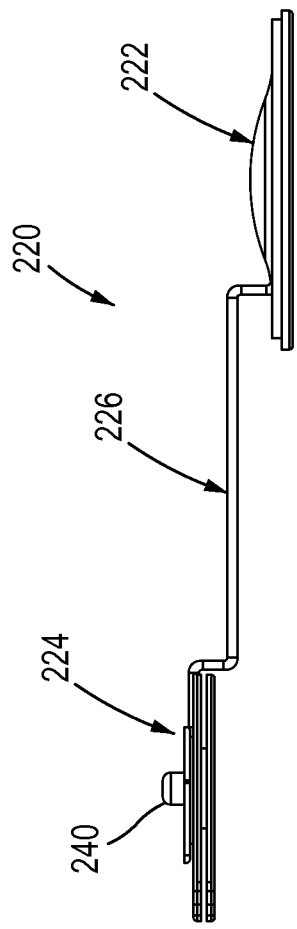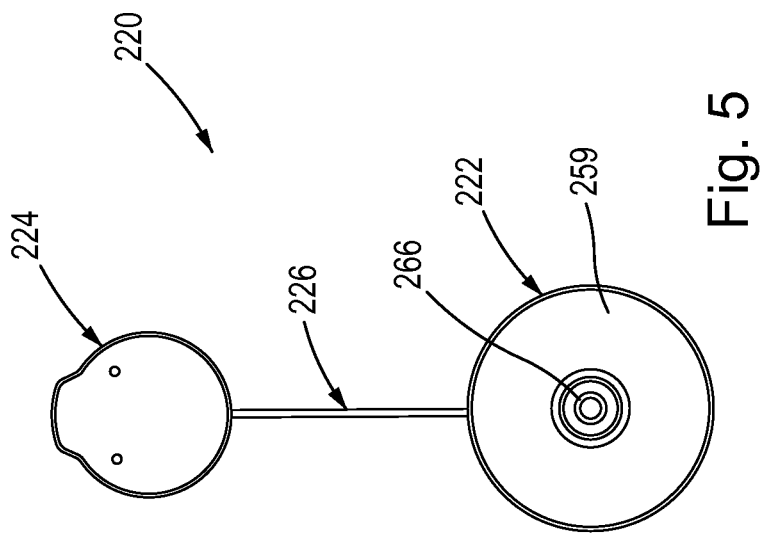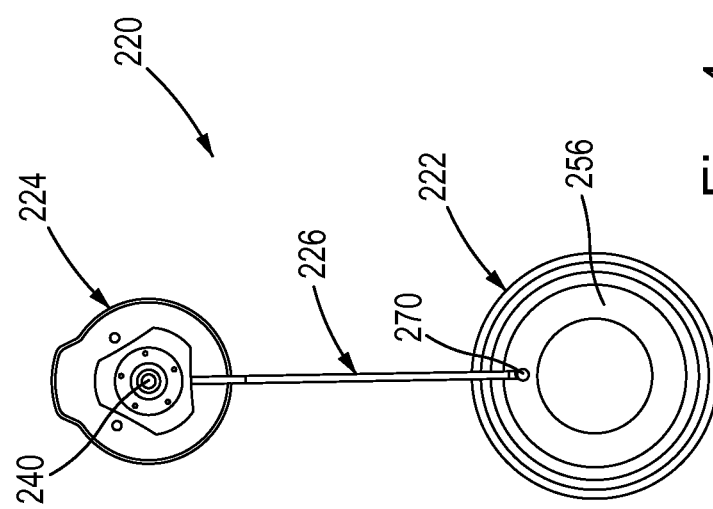

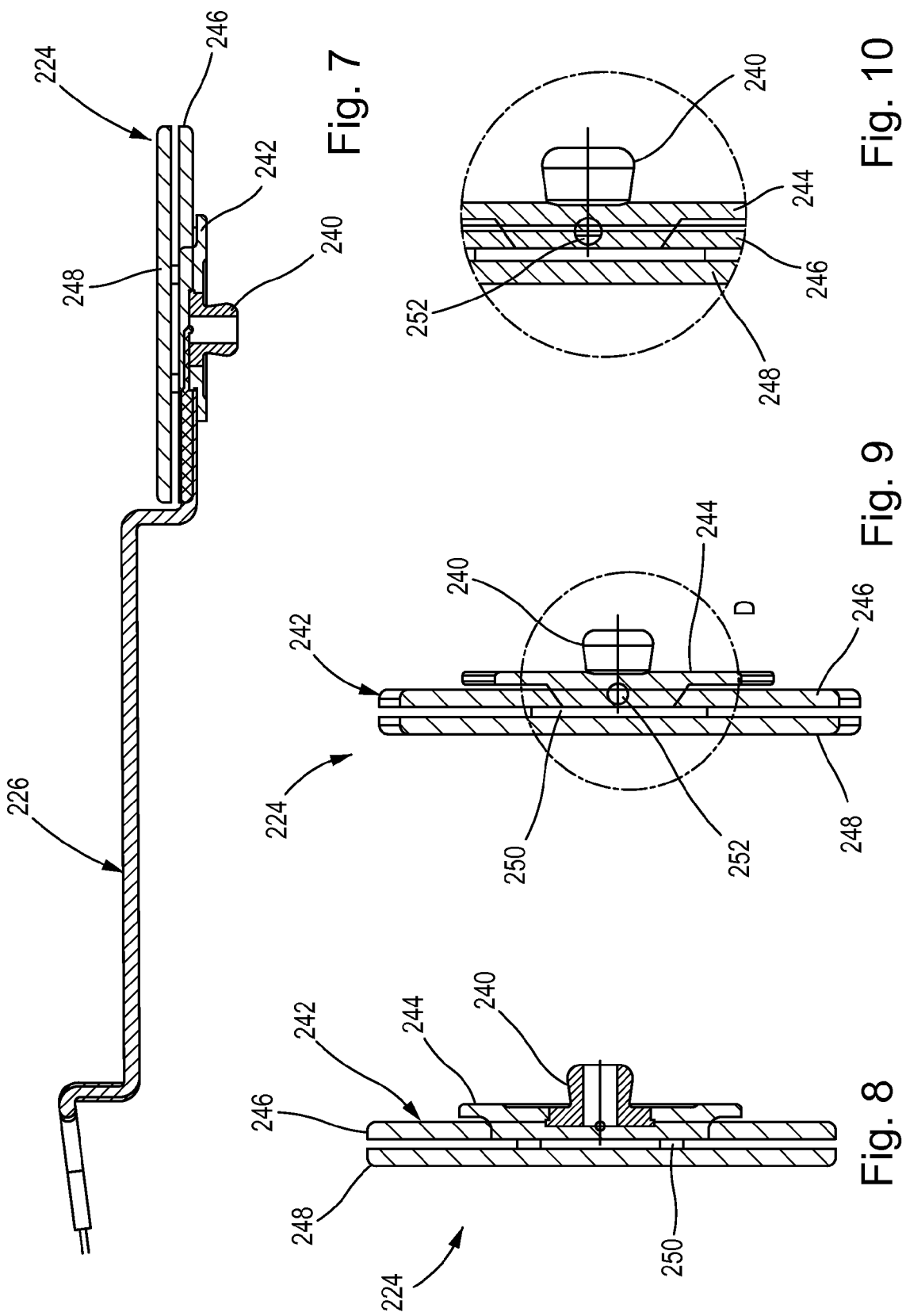

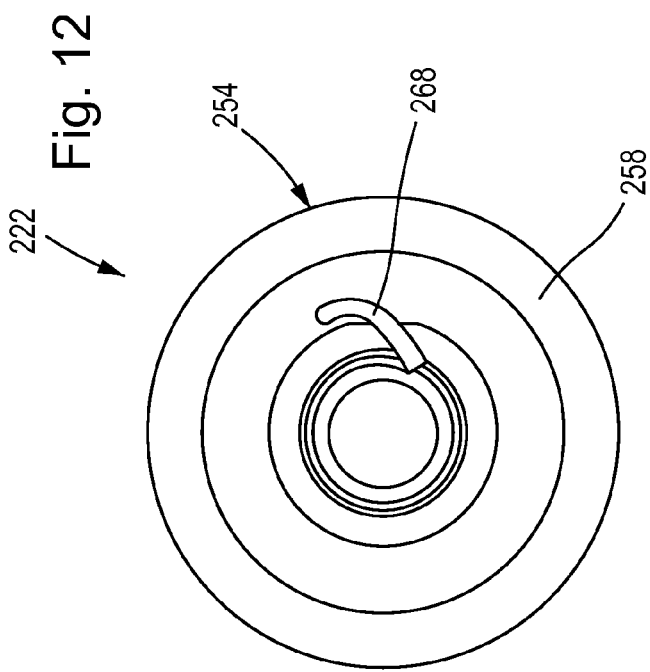
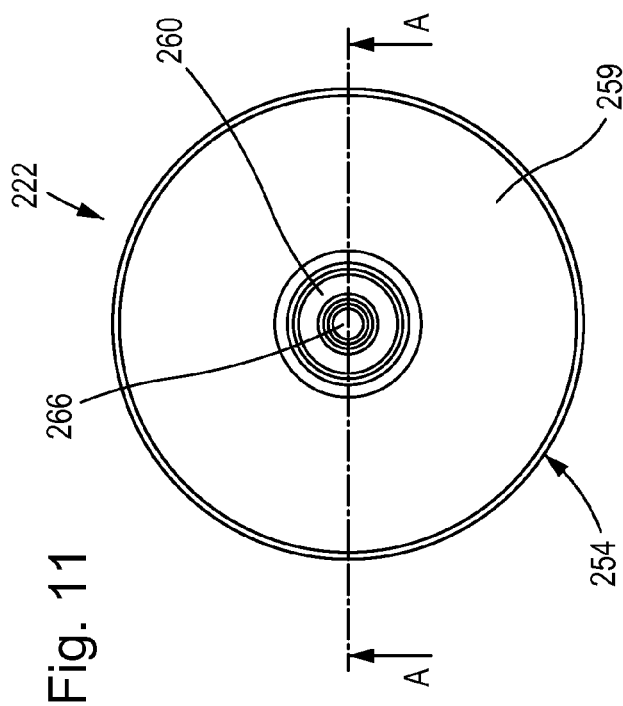
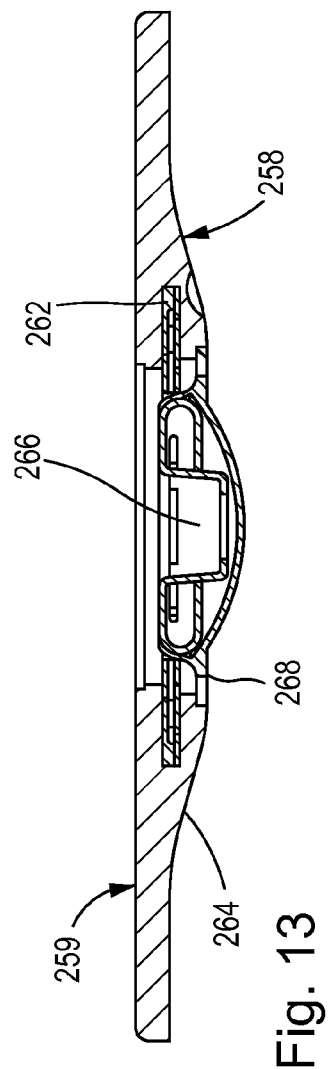
Fig. 12
Fig. 11
Fig. 13

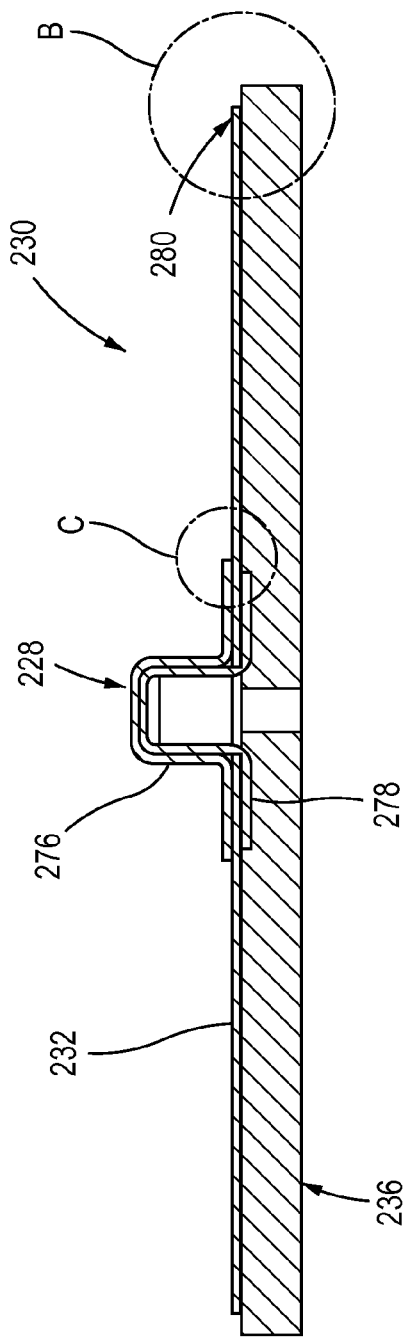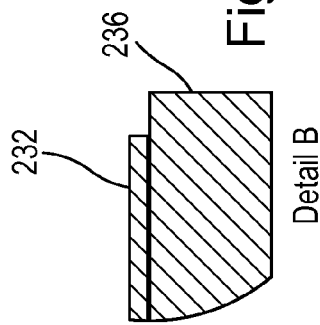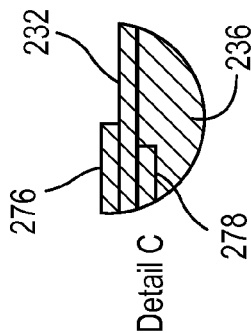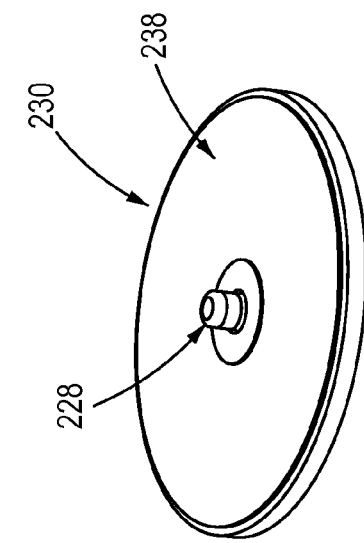

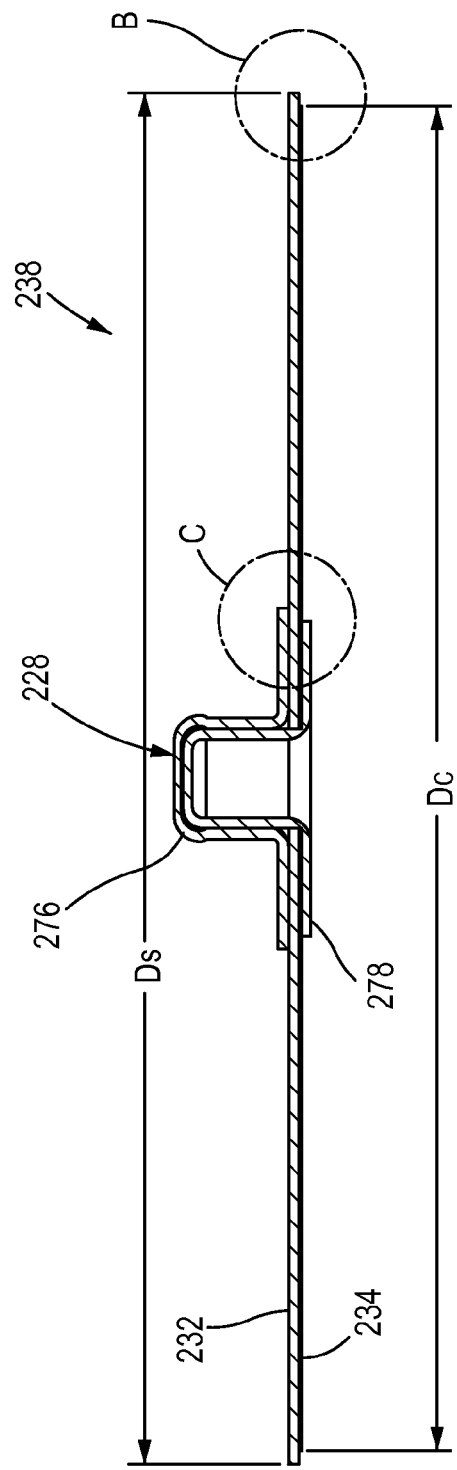
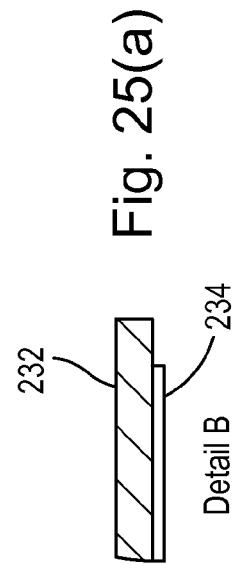
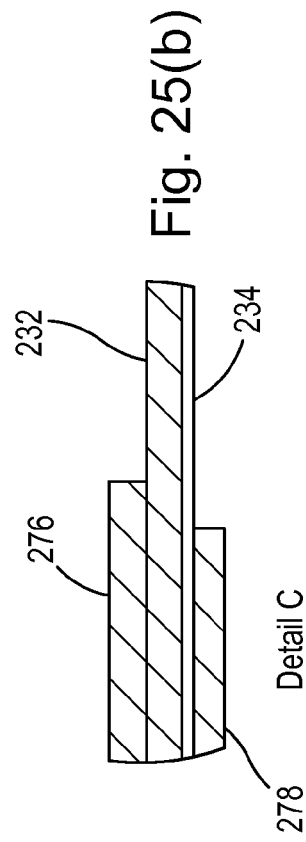
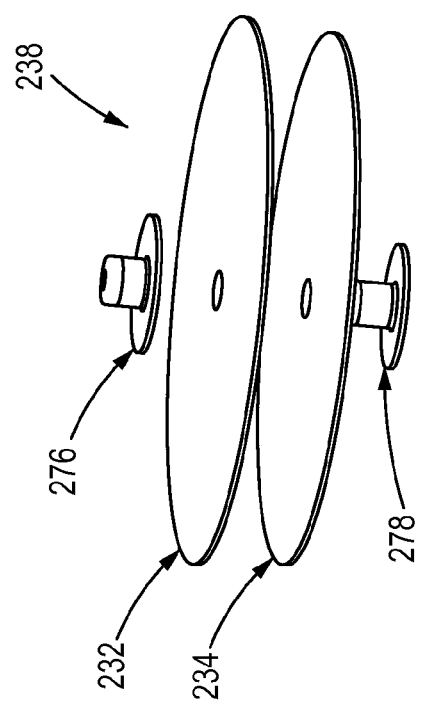

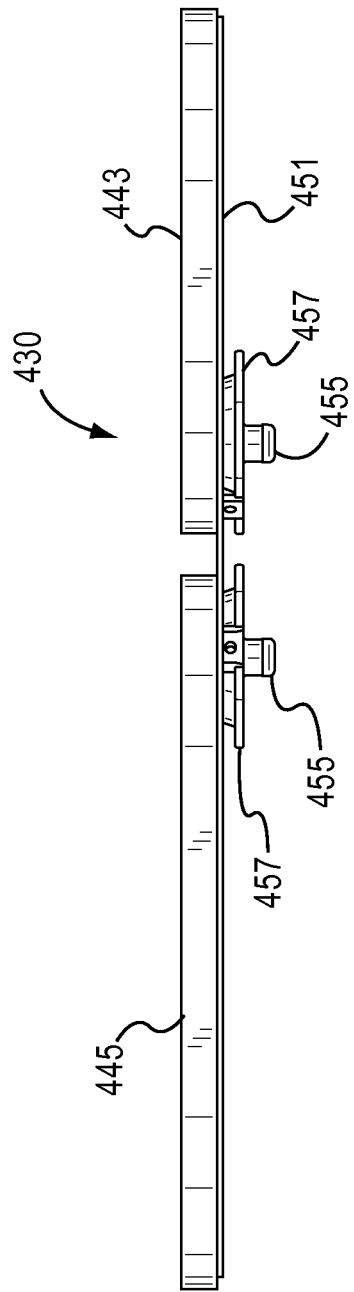
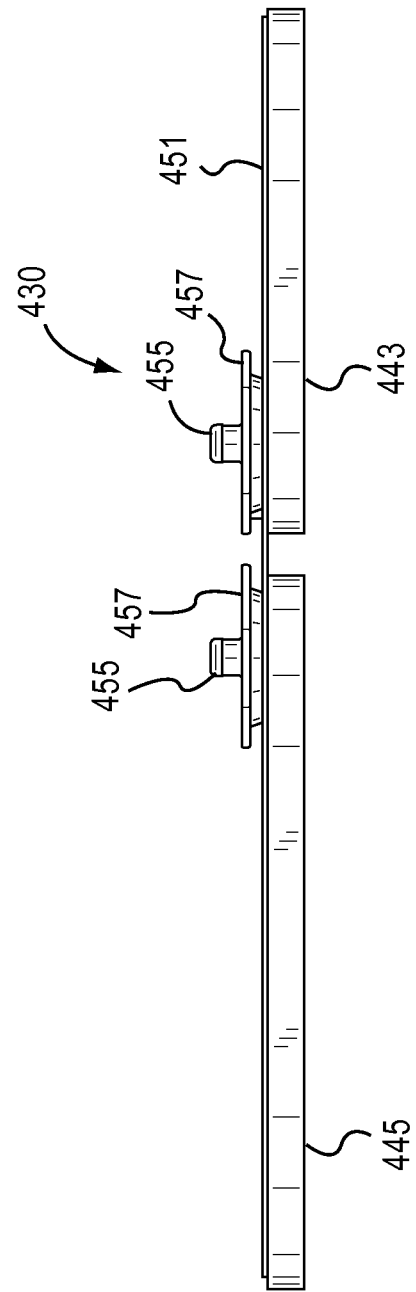

ELECTRODE FOR MUSCLE STIMULATION

BACKGROUND

The invention relates generally to medical devices and more particularly to an electrode kit for use in functional electrical stimulation treatment in conjunction with an orthosis.

An orthosis, such as a splint, cuff or garment, can be used in conjunction with an electrode to provide electrical stimulation of, for example, paralyzed limbs in therapeutic exercises and for generating limb function during functional electrical stimulation (FES). An electrode kit for such use can include, for example, a base portion that can be attached to an interior surface of an orthosis and an electrode assembly including an electrode and a pad that contacts the surface of the patient's skin. In such FES devices, the contact with the pad can cause irritation to the patient's skin. For example, many known FES devices include the use of hydro-gel electrodes that can cause skin irritation to the patient over prolonged use.

FES is a means to communicate with the neuromuscular system for producing contraction in muscles or sensory input to the body. FES can be used in neuroprostheses for restoring active function to paralyzed or plegic body limbs in patients suffering disease or trauma to the central nervous system, in neurological conditions such as stroke, spinal cord injury, head injury, cerebral palsy and multiple sclerosis. Surface FES systems use controlled electrical currents through electrodes placed on the surface of the body, in order to trigger contraction from muscles underlying the electrode or to input sensory stimulus. Surface neuroprostheses can coordinate the FES-activation of several muscles of the limb alone, or in coordination with voluntary activation of muscles under natural neurological control. Surface neuroprostheses are in use today for functional activities such as walking, standing, gripping/releasing objects, etc.

Activation of selected muscles of a limb by FES to generate controlled movements has been used, both as a therapeutic modality and for the improvement or restoration of activities of daily living (ADL) or functional restoration. Devices based on surface electrical stimulation which have been developed for activating specific body sites include, for example, the dropfoot system, which activates the ankle joint, modifying hemiplegic gait; hybrid FES-orthosis systems for restoring gait in spinal cord-injured patients, and systems for therapeutic activation and functional restoration of the hand.

In many of the known FES devices, replacement of dried-out pads and/or electrodes can be complex, making it difficult for a patient to perform without assistance. In addition, the location of the pad relative to the electrode is not always well-defined, producing a possible misalignment between the electrode and the motor point of the muscle, which can cause an undesirable overflow of the electrical stimulus. Thus, electrode placement is an important issue for surface neuroprostheses and involves accurately positioning the electrodes over the motor points of the muscles to be activated. Accurate electrode positioning can ensure activation of the correct muscle without overflow to unwanted muscles, sensory tolerance of the stimulation current intensity needed to produce the desired response, and the quality of the muscle contraction.

Thus, there is a need for an electrode and/or electrode kit for use in conjunction with an orthosis that can be easily and accurately attached to and removed from the orthosis by the clinician or by the patient. There is also a need for an electrode that provides patient comfort and reduces or eliminates skin reactions to the electrode.

SUMMARY OF THE INVENTION

Systems, devices and methods for treating a targeted body tissue (e.g., bone, soft tissue, muscle, ligaments, etc.) by stimulating the body tissue with an electric current are described herein. In one embodiment, an apparatus includes an electrode carrier configured to be removably coupled to an interior surface of an orthosis. The electrode carrier includes a recess configured to matingly receive a portion of an electrode. The electrode carrier is electrically coupled to the electrode when the portion of the electrode is disposed within the recess. A connection member is electrically coupled to the electrode carrier and is configured to be releasably coupled to a surface of the orthosis. The electrode carrier is electrically coupled to the orthosis when the connection member is coupled to the orthosis. In some embodiments, the electrode carrier is configured to be removably coupled to the interior surface of the orthosis. In some embodiments, at least a portion of the electrode is constructed of an absorptive material.

BRIEF DESCRIPTION OF THE DRAWINGS

FIG. 3 is a side view of a base of the electrode device of FIG. 2.

FIG. 4 is a top view of the base of FIG. 3.

FIG. 5 is a bottom view of the base of FIG. 3.

FIG. 7 is a cross-sectional view of the portion of the base of FIG. 6 taken along line B-B in FIG. 6.

FIG. 8 is a cross-sectional view of the portion of the base of FIG. 6 taken along line A-A in FIG. 6.

FIG. 9 is a cross-sectional view of the portion of the base of FIG. 6 taken along line C-C in FIG. 6.

FIG. 10 is an enlarged detail view of detail D in FIG. 9.

FIG. 11 is a bottom view of an electrode carrier of the base of FIG. 3.

FIG. 12 is a top view of the electrode carrier of FIG. 11.

FIG. 13 is a cross-sectional view of the electrode carrier of FIG. 11 taken along line A-A in FIG. 11.

FIG. 19 is a side cross-sectional view of an electrode assembly according to an embodiment.

FIG. 20 is a perspective view of the electrode assembly of FIG. 19.

FIG. 21 is an exploded view of the electrode assembly of FIG. 20.

FIG. 22(a) and FIG. 22(b) are enlarged views of detail B in FIG. 19 and detail C in FIG. 19, respectively.

FIG. 23 is a side cross-sectional view of a portion of the electrode assembly of FIG. 19.

FIG. 24 is an exploded view of the portion of the electrode assembly of FIG. 23.

FIG. 25(a) and FIG. 25(b) are enlarged views of detail B in FIG. 23 and detail C in FIG. 23, respectively.

FIG. 42 is a front end view of the electrode assembly of FIG. 35.

FIG. 43 is a rear end view of the electrode assembly of FIG. 35.

DETAILED DESCRIPTION

Devices, kits and methods are described herein that include an electrode kit and/or electrode device that can be used in conjunction with a surface neuroprosthesis device or orthosis for functional electrical stimulation (FES) and/or neuromuscular electrical stimulation (NMES) of a targeted body tissue (e.g., muscle, ligament), such as an impaired limb. For example, in some embodiments, such treatment includes the functional electrical stimulation of intact nerves of limbs to trigger a muscle contraction or response. In some embodiments, such treatment includes the functional stimulation of a targeted body tissue to provide sensory stimulation. A surface neuroprosthesis device or orthosis, can be for example, a cast, splint, cuff, wristlet, gauntlet, strap or other garment that can be worn by a patient and that has one or more electrodes coupled to the orthosis and is in contact with the skin of the patient.

An electrode kit or device as described herein can include, for example, a base and an electrode assembly couplable to the base. As described herein, the base of an electrode device can be coupled to the interior surface of an orthosis with, for example, VELCRO patches, press-studs, magnetic couplers, or specialized holders that press the conductive back of the electrode assembly against a conductive stud or panel inside the orthosis, or a combination thereof. The electrode devices described herein can be used in conjunction with a variety of different types of orthoses configured for various body limbs, such as, for example, devices used in functional electrical stimulation of a muscle of an upper limb, such as various locations on an arm, and for lower limbs, such as various locations on a leg.

As described herein, an electrode assembly that is configured to make electrical contact with the skin can include a conductive electrode assembly that is held onto a part of the body with the orthosis. In some embodiments, the electrode assembly includes a metal mesh conductor and an absorbent pad, all of which can be soaked in water. The electrode assembly can be releasably coupled to the electrode base of the electrode kit such that it can be easily removed and replaced as needed. The electrode assembly can be, for example, disposable.

Figure 1:
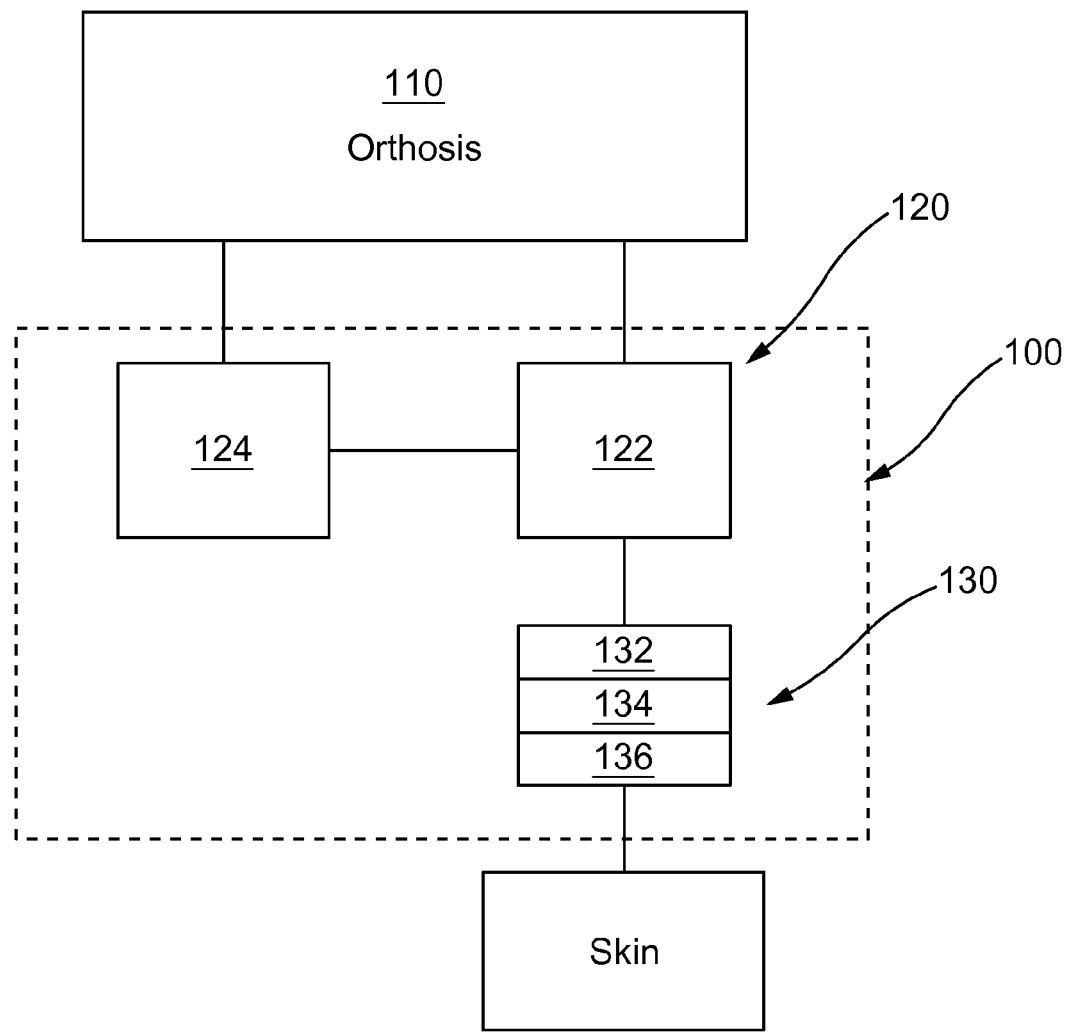
FIG. 1 is a schematic illustration of an electrode device according to an embodiment.

FIG. 1 is a schematic illustration of an embodiment of an electrode kit or device that can be used in conjunction with an orthosis to provide functional electrical stimulation to a target body tissue. An electrode device 100, includes a base 120 and an electrode assembly 130. The electrode device 100 is configured to be coupled to an orthosis 110, such as, for example, a cast, splint, cuff, wristlet, gauntlet, strap or other garment that can be worn by a patient. The orthosis 110, can be configured for use in electrical stimulation treatment at various locations on a patient's body, such as for example, a leg, foot, arm or hand. In some embodiments, multiple electrode devices are configured to be coupled to an orthosis 110. Various example embodiments of an orthosis and/or stimulation control systems that can be used in conjunction with an electrode device 100 as described herein are described in U.S. Pat. Nos. 6,829,510, 7,502,652, 7,146,220, 7,337,007 and 7,149,582, and International Patent Publication No. WO 03/051453, the disclosure of each of which is incorporated herein by reference in its entirety. Other example embodiments of orthosis devices and a stimulation control system that can be used in conjunction with the electrode devices described herein are described in co-pending U.S. patent application Ser. No. 13/022,149, bearing ("the '149 application"), the disclosure of which is incorporated herein by reference in its entirety.

The base 120 includes an electrode carrier 122 coupled to a connection member 124. The connection member 124 can be releasably coupled to the orthosis 110 at a desired location on an interior surface of the orthosis 110. The connection member 124 can include a base member (not shown in FIG. 1) and a coupling portion (not shown in FIG. 1). The coupling portion can be configured to be coupled to a mating coupling member disposed on the orthosis 110. In some embodiments, the coupling portion can also serve as the connecting terminal for the stimulating current. In some embodiments, the coupling portion of the connection member 124 includes a protrusion configured to be received within a recess defined in the orthosis 110 to form a snap-fit connection. In such an embodiment, although the connection member 124 is releasably coupled to the orthosis 110, it is stationary or fixed to the orthosis 110 during the electrical stimulation treatment.

In some embodiments, the base 120 can be coupled to a panel (not shown in FIG. 1) that can be releasably coupled to the orthosis 110. The panel can be provided as a layer between the inner surface of the orthosis 110 and the skin of the user/patient. The panel can include openings through which a coupling portion of the base 120 can be disposed such that it can be coupled to mating coupling member on the inner surface of the orthosis 110. The panel can be configured for a particular user/patient and can allow for a common orthosis 110 to be used on a variety of different users/patients. In some embodiments, the panel can be disposable. An embodiment of such a panel and electrode assembly are described in more detail below.

The electrode carrier 122 can be electrically coupled to the connection member 124 with an electrical lead or cable (not shown in FIG. 1). The electrode carrier 122 is also configured to be removably coupled to an interior surface of the orthosis 110 such that it can be repositioned at various locations on the orthosis 110 as needed during treatment. For example, the electrical lead can be flexible allowing the electrode carrier 122 to be moved relative to the connection member 124. The connection member 124 can be fixedly or releasably coupled to the orthosis 110 at a designated location, and the electrode carrier 122 can be coupled to the orthosis 110 at a different location than the connection member 124 such that it is at a spaced distance from the connection member 124. The electrode carrier 122 can be moved to different locations relative to the connection member 124 as needed. Through its electrical coupling to the connection member 124, the electrode carrier 122 is also electrically coupled to the orthosis 110 when coupled thereto.

In some embodiments, the electrode carrier 122 can be removably coupled to the orthosis 110 with a VELCRO attachment. For example, the electrode carrier 122 can include a first part of a VELCRO attachment member and a second mating part can be attached to the orthosis 110. Such an attachment method is described in more detail below with reference to specific embodiments.

In some embodiments, the electrode carrier 122 can be coupled to the orthosis 110 with, for example, a snap fit coupling. In some such embodiments, the snap-fit coupling can also provide an electrical connection to the orthosis 110. In some embodiments, the base 120 does not include a connection member 124. In some such embodiments, the electrode carrier 122 can include two coupling portions to couple the electrode carrier 122 to the orthosis 110.

The electrode assembly 130 is configured to be coupled to the electrode carrier 122. In some embodiments, the electrode assembly 130 is removably coupled to the electrode carrier 122. For example, in some embodiments, the electrode carrier 122 defines a recess configured to matingly receive a portion of the electrode assembly 130 forming a snap-fit coupling. The removable coupling of the electrode assembly 130 to the electrode carrier 122 allows for the electrode assembly 130 to be easily removed and/or replaced as needed. The electrode assembly 130 can also be disposable. Because the electrode assembly 130 is easily removable, the user (e.g., patient) can remove and replace the electrode assembly 130, for example, after two weeks, rather than requiring a clinician or specialist. In some embodiments, the user can remove the electrode assembly 130 more frequently, such as for example, on a daily basis to wet the electrode assembly 130. The removability and disposability of the electrode assembly 130 also helps reduce or eliminate "scale" build up on the electrode that can occur after prolonged use.

The electrode assembly 130 can include a support frame 132, a conductor member 134 and a pad 136. The support frame 132 can be formed in part with a substantially rigid material, such as a suitable plastic material, and include a coupling portion that can be releasably and electrically coupled to the electrode carrier 122. For example, the support frame 132 can include a protrusion (not shown in FIG. 1) configured to be matingly received within a recess of the electrode carrier 122 to form a snap-fit connection. The protrusion can be formed integrally with the support frame 132 or be provided as a separate component. The support frame 132 can be formed, for example, with a polypropylene, a polyvinyl or a mixture thereof.

The pad 136 can be coupled to a surface of the support frame 132. The conductor member 134 can also be coupled to the same surface of the support frame 132 such that it is disposed between the support frame 132 and the pad 136. For example, the pad 134 can be ultrasonically welded around a perimeter portion of the surface of the support frame 132, sandwiching the conductor member 134 therebetween. With the conductor member 134 disposed below the pad 136, the electrical stimulation can be more evenly spread across the pad 136 during FES or NMES treatment. The conductor member 134 can be formed with, for example, a stainless steel material. The conductor member 134 can be shaped substantially similar to the shape of the pad 136. In some embodiments, the conductor member 134 is circular or disc shaped.

The pad 136 can include at least a portion that includes an absorptive material, such as, for example, a cloth, felt, velvet, a non-woven viscose, or other suitable material that is absorptive of liquids, gels, etc. The absorptive material of the pad 136 allows the pad 136 to be soaked with liquid (e.g., water) in preparation for use, as described in more detail below. In some embodiments, the pad 136 can be porous and/or include holes to enable faster absorption of the liquid. In some embodiments, the pad 136 can include a thin membrane that can reduce and/or prevent the liquid from evaporating quickly. The pad 136 is configured to contact the skin of the patient during treatment, and therefore, it is desirable to be formed with a material that will provide comfort to the patient and reduce the possibility of irritation to the patient's skin. The conductor member 134 can be, for example, formed with a fine metallic wire mesh.

In use, the connection member 124 can be releasably or fixedly coupled to the orthosis 110 such that it is stationary during the electrical stimulation treatment. For example, the connection member 124 can be snapped into the orthosis 110 providing an electrical connection to the orthosis 110 for the electrical stimulation. The electrode assembly 130 is soaked with water until it is saturated and the excess water is wiped or blotted off the support frame side of the electrode assembly 130 where the coupling portion of the electrode assembly 130 is disposed. The electrode assembly 130 is then coupled to the electrode carrier 122. The electrode carrier 122 can be coupled to the orthosis 110 before or after the electrode assembly 130 is coupled to the electrode carrier 122. The electrode carrier 122 is coupled to the orthosis 110 at a desired location such that the electrode assembly 130 is positioned at the targeted treatment site when the orthosis 110 is placed on the patient's body. For example, as described above, the electrode carrier 122 can be coupled to the orthosis 110 with a VELCRO attachment. The above procedure can be performed to couple a second (or more) electrode kit to the orthosis 110.

With the electrode device 100 in place on the orthosis 110, the orthosis 110 can be placed on the user to provide FES treatment or NMES treatment to the targeted treatment site. Examples of a stimulation system that can be used to activate the functional electrical stimulation of the orthosis 110 are described, for example, in International Patent Publication No. WO 03/051453, and the '149 application, incorporated by reference above.

If at a subsequent time the desired treatment site has changed, the patient and/or clinician can decouple the electrode carrier 122 from the orthosis 110 and reposition it at a different location. Thus, the movability of the electrode carrier 122 allows for easy repositioning of the electrode assembly 130 to a desired target treatment site. In addition, the releasable attachment of the electrode assembly 130 to the electrode carrier 122 allows for the patient and/or clinician to easily remove the electrode assembly 130 from the electrode carrier 122 as needed. Thus, the electrode assembly 130 can be disposable and as the pad 136 becomes dried out or worn, it can be easily discarded and replaced.

To replace the electrode base 120, the user turns off the system and then disconnects the connection member 124 from the orthosis 110, terminating the electrical connection. The electrode carrier 122 can be removed as described above. A new electrode base 120 can then be coupled to the orthosis 110. The same or new electrode assembly 130 can be coupled to the new electrode base 120 as described above. Prior to removing the electrode base 120, the position of the electrode base 120 on the orthosis 110 can be marked, using for example, a marking tool such as a pen, pencil, etc., such that the new electrode base 120 can be positioned on the orthosis 110 at the same location.

Having described above various general principles, several examples of various embodiments of these concepts are now described. These embodiments are only examples, and many other configurations of an electrode kit and/or the various components of am electrode kit are contemplated.

Figure 2:
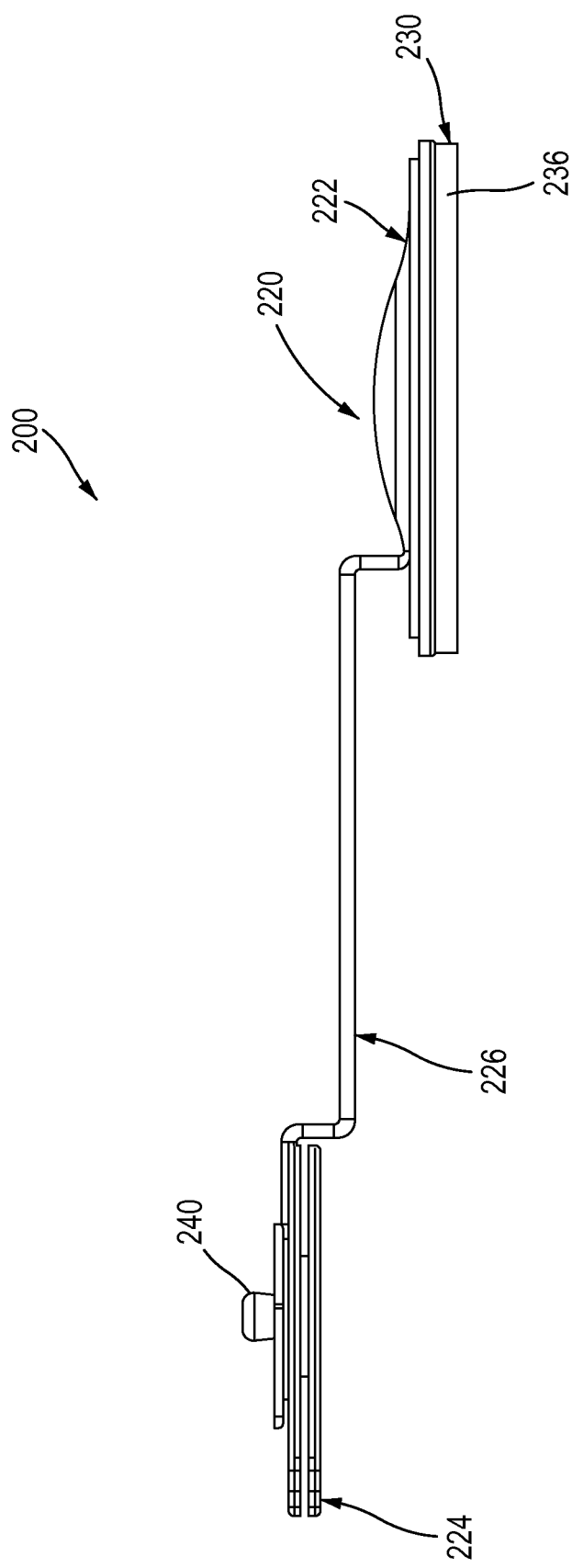
FIG. 2 is a side view of an electrode device according to an embodiment.
Figure 6:
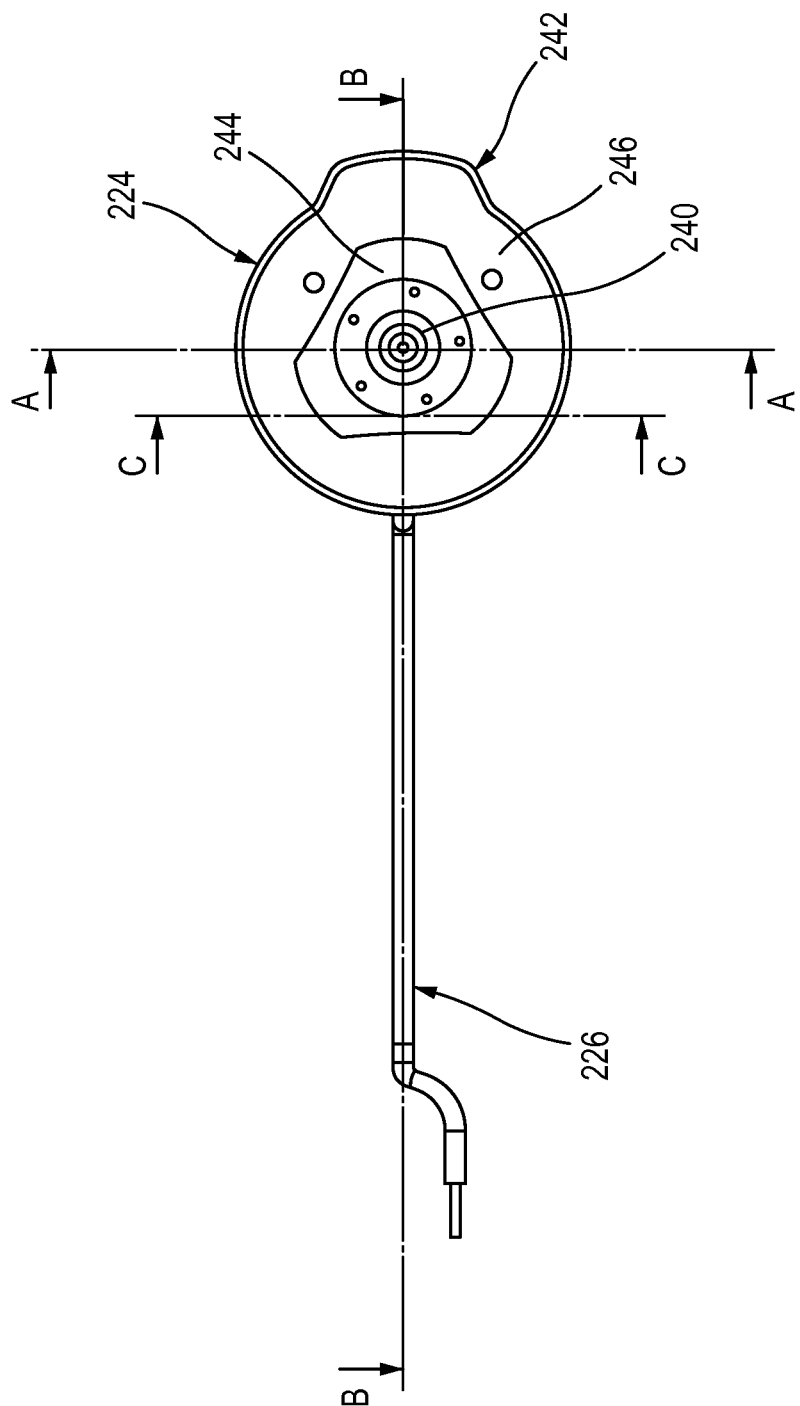
FIG. 6 is a top view of a portion of the base of FIG. 3.

FIG. 2 illustrates an electrode kit according to an embodiment. An electrode kit or device 200 includes an electrode base 220 and an electrode assembly portion 230 releasably coupled thereto. As described above, one or more electrode devices 200 can be coupled to an orthosis and used to provide functional electrical stimulation to a targeted treatment site on a patient.

The electrode base 220 includes an electrode carrier 222, a connection member 224, and an electrical lead or cable 226 (as best shown in FIGS. 3-5). As shown in FIGS. 6-10, the connection member 224 includes a coupling portion 240 coupled to a frame assembly 242. In this embodiment, the coupling portion 240 is a protrusion configured to be received within an opening defined in an orthosis (not shown) to releasably couple the base 220 to the orthosis with a snap-fit connection. The frame assembly 242 includes a first member 244, a second member 246, a third member 246 and a pronged connector 250. The components of the frame assembly 242 can be coupled together with, for example, adhesive, ultrasonic welding, over-molding, or other known methods. The first member 244 defines an opening 252 configured to receive an end portion of the electrical lead 226 to couple the lead 226 to the connection member 224.

Figure 14:
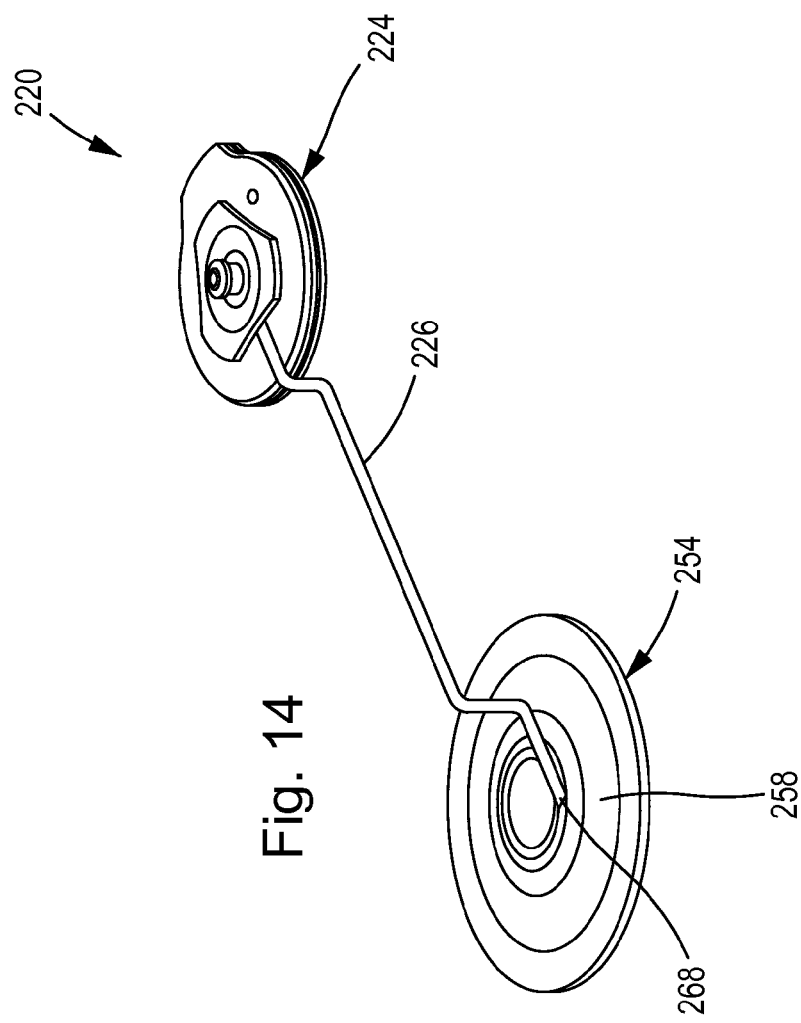
FIG. 14 is a perspective view of a portion of the base of FIG. 3.

The electrode carrier 222 includes a carrier base assembly 254 (see e.g., FIGS. 11-13) and an orthosis attachment member 256 (shown in FIG. 4). In this embodiment, the orthosis attachment member 256 is a VELCRO disc coupled to a first surface 258 (see e.g., FIG. 14) of the carrier base assembly 254. FIG. 14 illustrates the electrode base 220 with the orthosis attachment member 256 removed for illustrative purposes. The orthosis attachment member 256 can be, for example, sewn around a perimeter portion of the first surface 258 of the carrier base assembly 254. In some embodiments, the orthosis attachment member 256 can be adhesively coupled to the first surface 258. The orthosis attachment member 256 also defines an opening 270 configured to receive the electrical lead 226 therethrough, as shown in FIG. 4. The orthosis attachment member 256 can be used to removably couple the electrode carrier 222 to the orthosis at one or more locations. For example, the orthosis can include one or more discrete mating VELCRO attachment portions configured to matingly couple to the VELCRO orthosis attachment member 256. In some embodiments, the orthosis can include a continuous mating VELCRO attachment portion disposed on a surface of the orthosis such that the orthosis attachment member 256 can be moved to different locations on the orthosis as needed or desired. The removable coupling of the electrode carrier 222 to an orthosis is described in more detail below.

Figure 15:
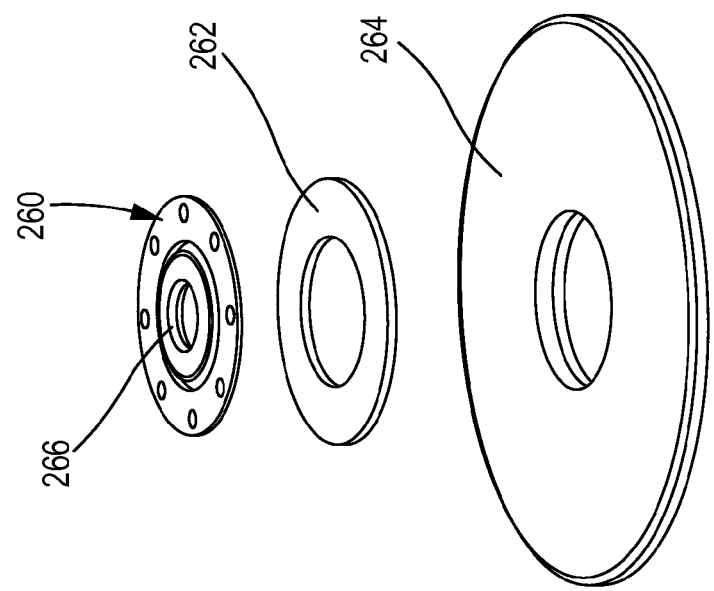
FIG. 15 is an exploded view of a portion of the electrode carrier of FIG. 11.

The carrier base assembly 254 includes a coupling member 260, a first member 262 and a second o member 264 (see e.g., FIG. 15, which illustrates an exploded perspective view of each of the components of the carrier base assembly 254). The coupling member 260 defines an opening or recess 266 configured to receive a protrusion defined by the electrode assembly 230 and provide a releasable snap-fit coupling (the electrode assembly 230 is described in more detail below). As shown, for example, in FIGS. 11-13, the carrier base assembly 254 has a second surface 259 on which the electrode assembly 230 is disposed when coupled to the carrier base assembly 254. The coupling member 260 also defines a groove 268 on the first surface 258 configured to receive an end portion of the electrical lead 226 to electrically couple the electrode carrier 222 to the connection member 224.

Figure 18A:
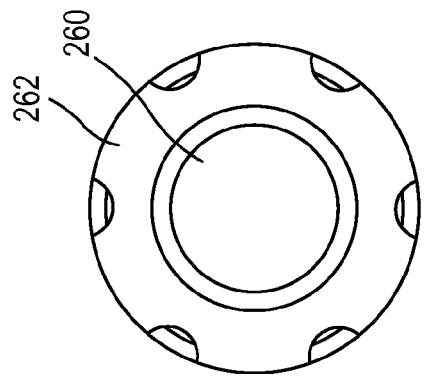
FIGS. 18(a), 18(b) and 18(c) are a top view, side view and bottom view, respectively, of a portion of the electrode carrier of FIG. 11.
Figure 18B:
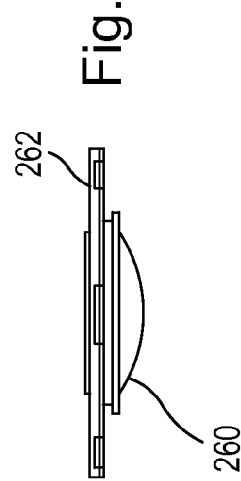
Figure 18C:
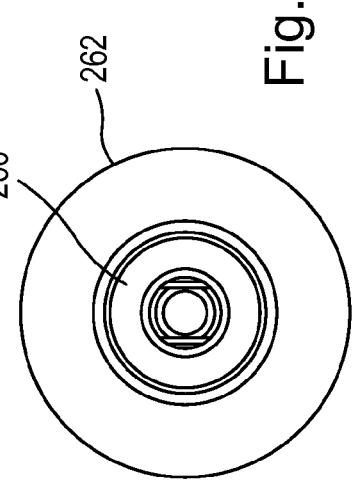
Figure 16:
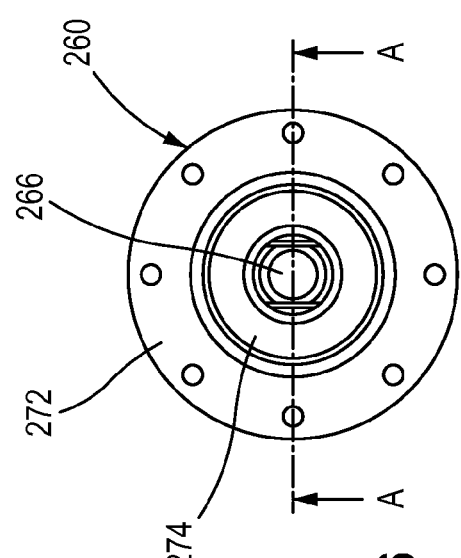
FIG. 16 is a bottom view of a portion of the electrode carrier of FIG. 11.
Figure 17:
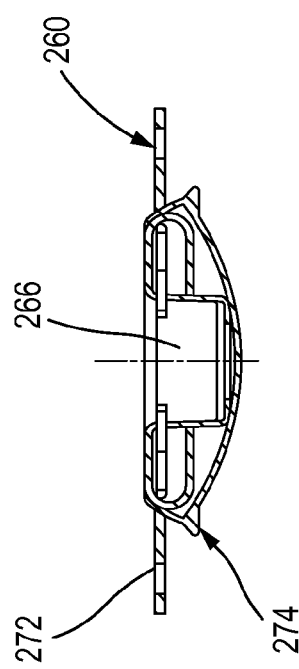
FIG. 17 is a cross-sectional of the portion of the electrode carrier of FIG. 16 taken along line A-A in FIG. 16.

The coupling member 260, the first member 262 and the second member 264 can be coupled together, for example, with an over-mold process. FIGS. 16 and 17 illustrate the coupling member 260 and FIGS. 18(a)-18(c) illustrate the first member 262 coupled to the coupling member 260 (prior to the second member 264 being coupled thereto). The coupling member 260 includes a support plate 272 and spring 274 that can be, for example, welded together.

FIGS. 19-25(c) illustrate the electrode assembly 230. The electrode assembly 230 includes a frame assembly 238 and an electrode pad 236. The electrode pad 236 can be formed at least in part with an absorptive material, such as, for example, felt. The pad 236 can be, for example, coupled to the frame assembly 238 with ultrasonic welding, described in more detail below.

As shown in FIGS. 23 and 24, the frame assembly 238 includes a support frame 232, a conductor member 234, and a coupling member 228 that includes a snap stud 276 and a snap post 278. The snap stud 276 defines an opening configured to receive the snap post 278 in a snap fit connection. The snap stud 276 and the snap post 278 are configured to be coupled together such that the support frame 232 and the conductor member 234 are sandwiched together as shown in FIG. 23. When assembled, the coupling member 228 provides a protrusion to be received in a mating recess or opening (e.g., opening 266) of the electrode carrier 222 as described in more detail below. The conductor member 234 can be formed with, for example, with a stainless steel metallic mesh and the support frame 232 can be formed with, for example, a suitable plastic material, such as polypropylene or polyvinyl or a mixture thereof. In one example, the support frame 232 can have, for example, a diameter Ds of 43.5 mm and the conductor member 234 can have a diameter Dc of for example 42.5 mm, as shown in FIG. 23.

The pad 236 is formed with an absorptive material, such as felt, cloth, velvet, viscose, etc., such that the pad 236 can be saturated with liquid (e.g., water) prior to use. The pad 236 can be coupled to the support frame 232 about a perimeter portion, as shown for example at location 280 in FIG. 19. For example, the pad 236 can be ultrasonically welded to the plastic support frame 232 such that a perimeter portion of the pad 236 overhangs the support frame 232 as shown, for example, in FIGS. 19 and 22(a). The conductor member 234 will then be disposed between the pad 236 and the support frame 232. The location of the conductor member 234 below the pad 234 allows for the electrical stimulation during the FES treatment to be distributed evenly across the pad 236 and to the target treatment site.

The coupling member 228 of the electrode assembly 230 is used to releasably couple the electrode assembly 230 to the electrode carrier 222 of the base assembly 220. Specifically, the snap post 276 of the coupling member 228 is configured to be received within the opening 266 of the electrode carrier 222 to releasably couple the electrode assembly 230 to the electrode carrier 222 with a snap-fit connection. As described previously, the electrode assembly 230 is soaked in water prior to being coupled to the electrode carrier 222 such that the absorptive material of the pad 234 is saturated with water.

In alternative embodiments, the coupling member 228 can include a magnet element (not shown). For example, the magnet element can be disposed adjacent to the snap stud 276 and can be used to help locate and/or align the coupling member 228 to the mating opening of the electrode carrier 266 of the electrode carrier 222. In some embodiments, magnetic coupler can be used in place of the snap-fit coupling member 228. For example, a magnetic coupling member can be disposed on the electrode assembly 230 or the electrode carrier 222 that can be magnetically coupled to a magnetically attracted coupling member (e.g., a metallic member) on the other of the electrode assembly 230 or the electrode carrier 222. In some embodiments, the magnetic coupler can provide the conductive medium of the electrode assembly. In some embodiments, and electrode assembly 230 can include one or more snap-fit coupling members and one or more magnetic coupling members.

Figure 26:
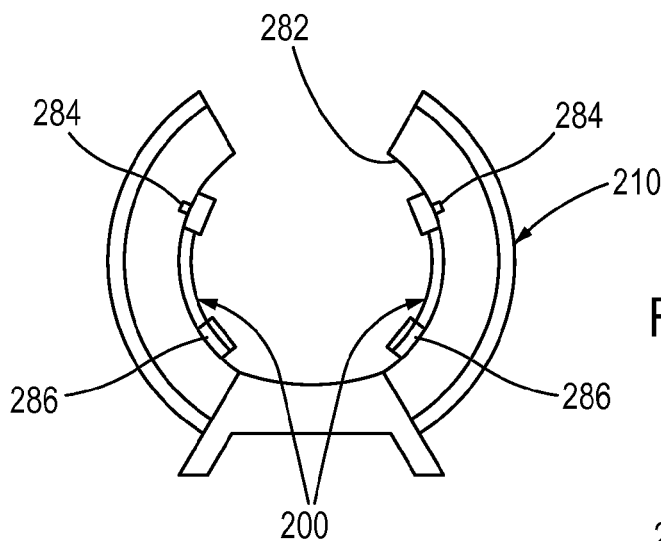
FIG. 26 is a side view of an orthosis and electrode devices according to an embodiment.
Figure 27:
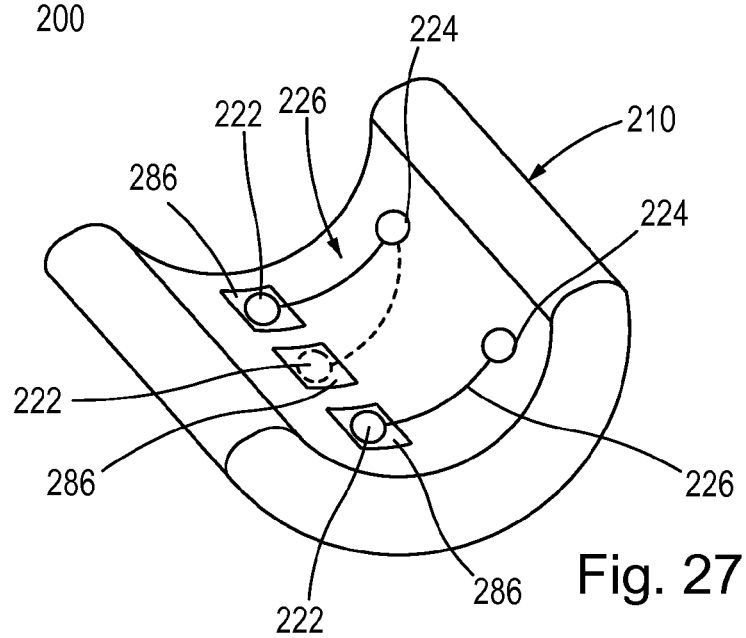
FIG. 27 is a perspective view of a portion of the orthosis and electrode devices of FIG. 26.

FIGS. 26 and 27 illustrate a portion of an orthosis 210 that can be used in conjunction with one or more electrode devices 200. The orthosis 210 is a cuff style orthosis that can be used, for example, for functional electrical stimulation treatment of an arm or leg. The orthosis 210 includes an interior surface 282 on which the electrode device 200 (or multiple devices 200) can be coupled. The orthosis 210 defines recesses 284 configured to matingly receive the coupling member 240 (i.e., protrusion) of the connection member 224. As described above, the coupling member 240 can be snap-fit into the recess 284 to provide a releasable snap-fit coupling of the connection member 224 to the orthosis 210 and provide an electrical connection to the orthosis 210 for the electrical stimulation. The orthosis 210 also includes at least one VELCRO attachment portion 286 configured to matingly couple to the VELCRO orthosis attachment member 256 of the electrode carrier 222.

In use, the electrode assembly 230 is soaked with water until it is saturated and the excess water is wiped or blotted off the support frame 232 of the electrode assembly 230. The electrode assembly 230 is then coupled to the electrode carrier 222 of the electrode base assembly 220 either before or after the electrode carrier 222 is coupled to the orthosis 210. With the electrode device 200 in place on the orthosis 210, the orthosis 210 can be placed on the user to provide FES treatment to the targeted treatment site.

If needed, the patient and/or clinician can decouple and reposition the electrode carrier 222 on the orthosis 210 as illustrated in FIG. 27 by the dashed-line version of the electrode device 200. In addition, the releasable attachment of the electrode assembly 230 to the electrode carrier 222 allows for the patient and/or clinician to easily remove the electrode assembly 230 from the electrode carrier 222 as needed. The entire base 220 can also be removed and replaced as needed as described previously.

Figure 28:
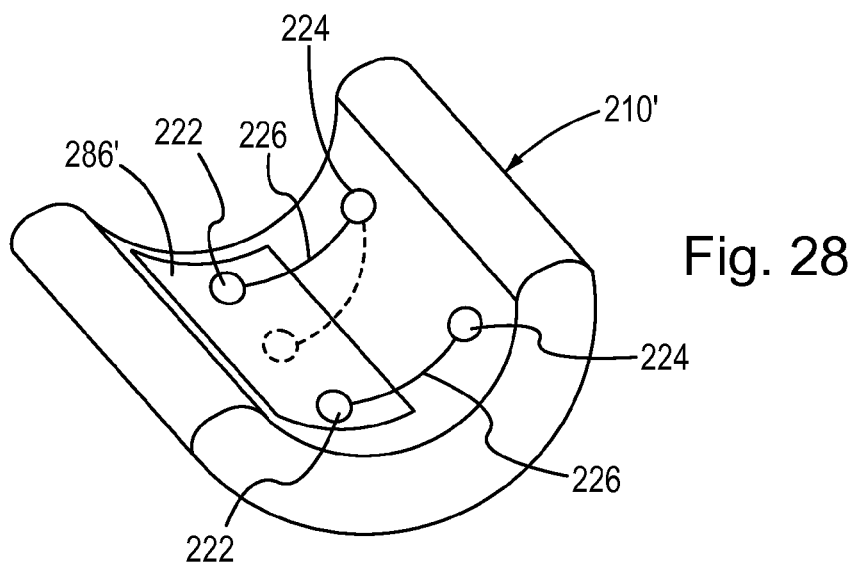
FIG. 28 is a perspective view of an other embodiment of an orthosis and an electrode device.

FIG. 28 illustrates a portion of another embodiment of an orthosis that can be used in conjunction with the electrode device 200. In this embodiment, an orthosis 210' defines a recess (not shown) configured to matingly receive the coupling member 240 as described above for orthosis 210. In this embodiment, the orthosis 210' includes a mating VELCRO attachment 286' in the form of a continuous sheet that allows for the electrode carrier 222 to be removably coupled to a variety different locations on the VELCRO attachment 286'. The dash-line version of the electrode device 200' illustrates the electrode carrier 222 being moved to different locations on the orthosis 210' while the connection member 224 remains stationary.

Figure 29:
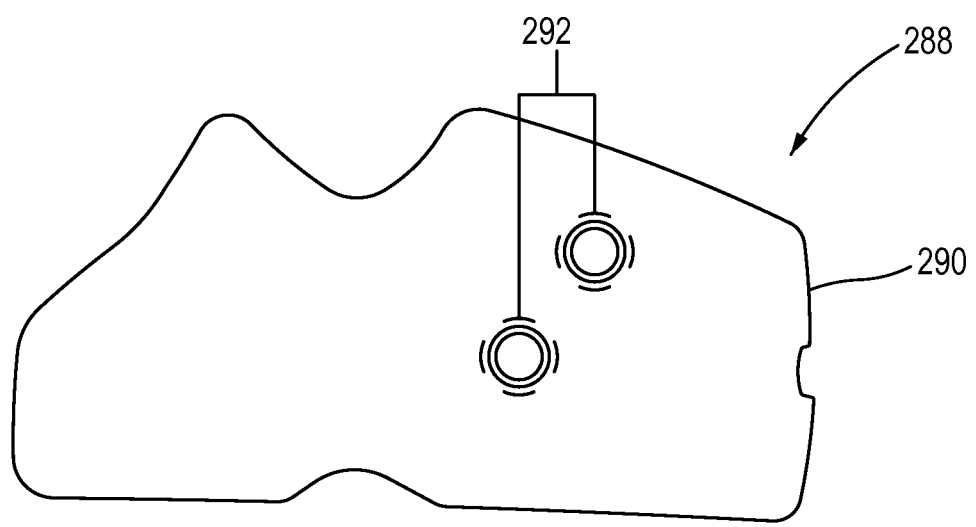
FIG. 29 is a front view of a panel that can be used with an electrode device, according to an embodiment.
Figure 30:
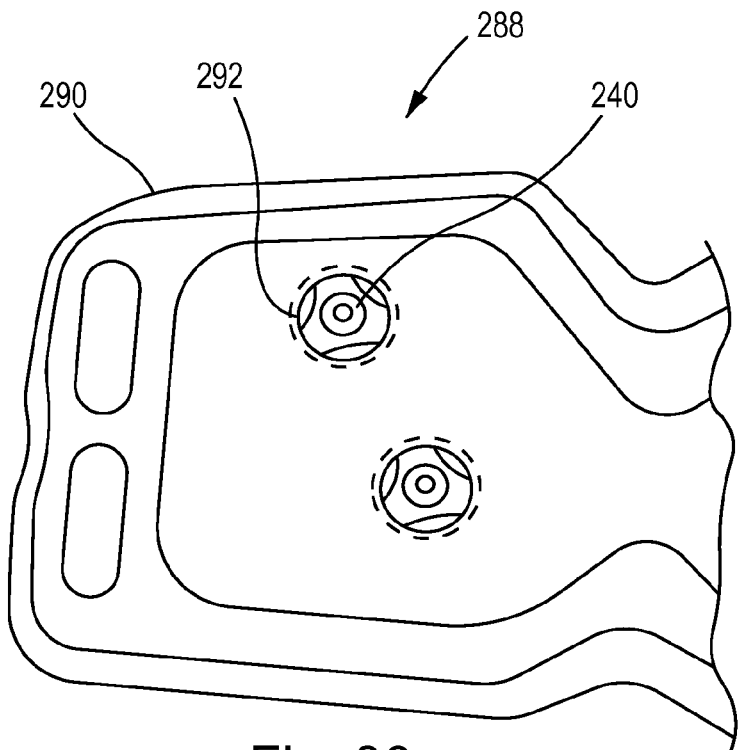
FIG. 30 is a back view of a portion of the panel of FIG. 29.

FIG. 29 illustrates an embodiment of a panel that can optionally be used in conjunction with an electrode device, such as, electrode device 200. A panel 288 includes a panel member 290 that defines two openings 292. The panel member 290 can be formed with a flexible material that can conform to the inner surface of an orthosis. The panel member 290 can be formed, for example, with a fabric, cloth, felt, velvet, or other suitable material. Each of the openings 292 can receive a coupling member 240 (i.e., protrusion) of a connection member 224 of an electrode device 200, as shown in FIG. 30. Thus, in this example embodiment, two electrode devices 200 can be coupled to the panel 288. Although FIGS. 29 and 30 illustrate the panel member 290 defining two openings 292, it should be understood that in other embodiments a panel member 290 can include less or more openings configured to receive a coupling member of an electrode assembly.

Figure 31:
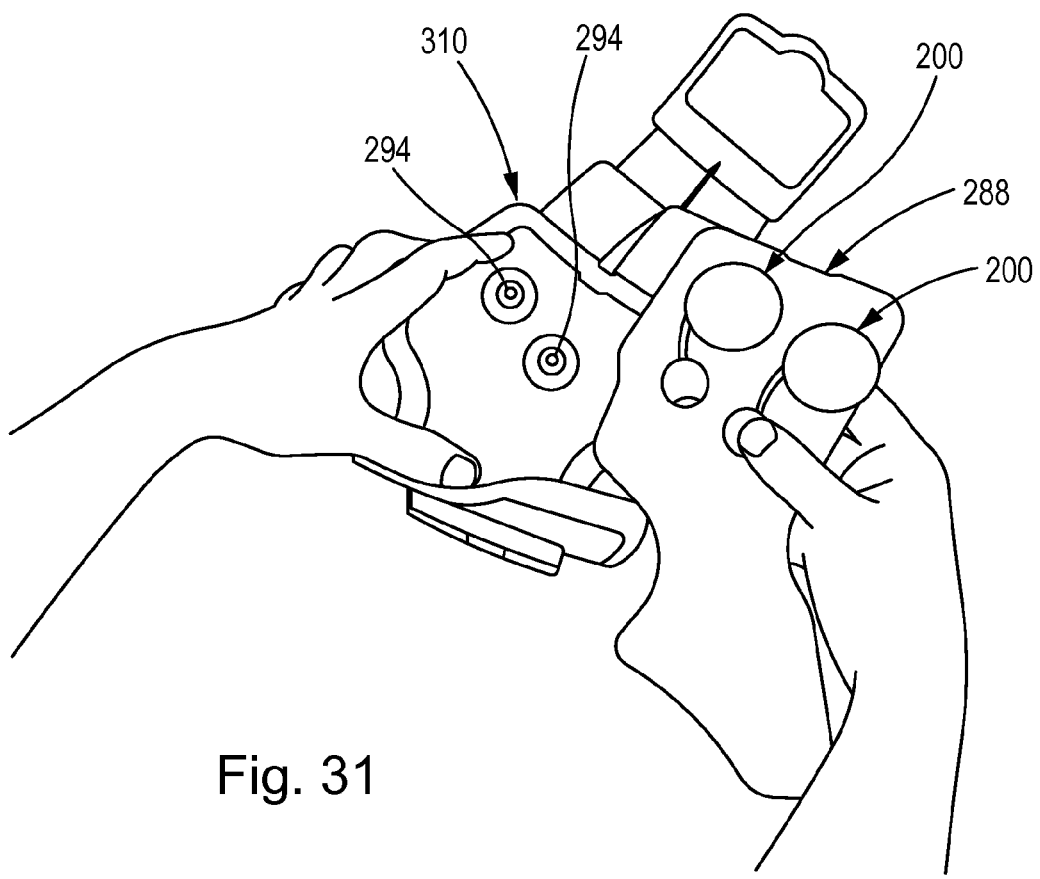
FIG. 31 is an illustration of the panel of FIG. 29 shown with electrode devices coupled thereto and an orthosis device to which the panel and electrode devices can be coupled.

The panel 288 can be releasably coupled to an orthosis device 310 (see e.g., FIG. 31). For example, one or more electrode devices 200 can be coupled to the panel 288 and the coupling portion 240 of the electrode device 200 (extending through the openings 292) can be coupled to a mating snap-fit coupler 294 on the orthosis device 310. The panel 288 can also include a coupling member (not shown), such as a VELCRO attachment member configured to be coupled to a mating VELCRO attachment (not shown) on the inner surface of the orthosis device 310. In some embodiments, additional snap-fit couplings and/or magnetic couplings can be used to couple the panel 288 to the orthosis device 310.

The panel 288 can be configured to fit a particular patient/user of the electrode device 200 and orthosis device 310. Thus, the orthosis device 310 can be a common size and the panel 288 can be sized and configured to accommodate the orthosis 310 to fit different patients/users. The panel 288 (and electrode assemblies coupled thereto) can be removed and re-coupled to the orthosis device 310 as needed.

Figure 32:
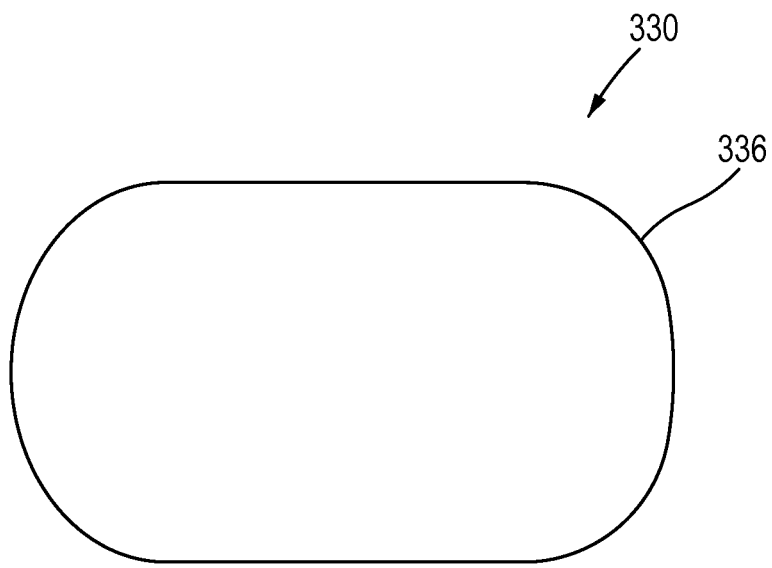
FIG. 32 is a front view of an electrode assembly according to another embodiment.
Figure 33:
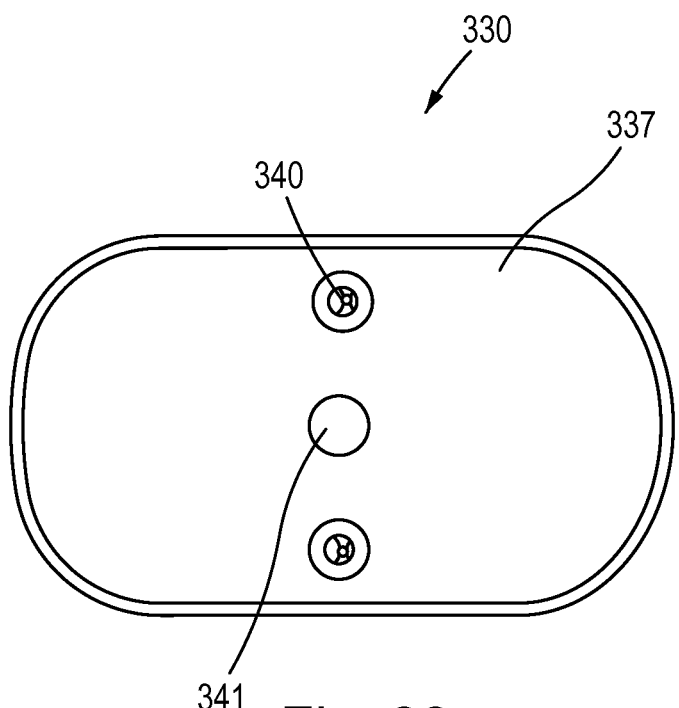
FIG. 33 is a back view of the electrode assembly of FIG. 32.
Figure 34:
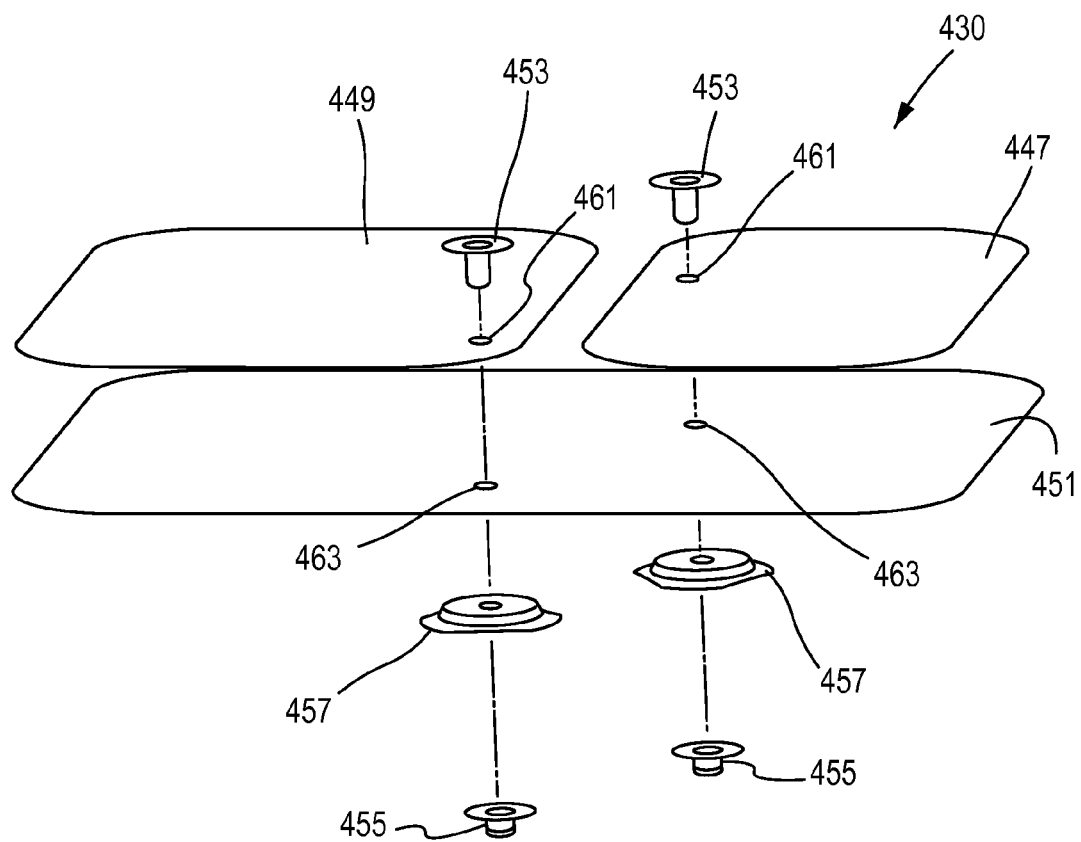
FIG. 34 is an exploded view of a portion of an electrode assembly according to an embodiment.

FIGS. 32 and 33 illustrate another embodiment of an electrode device. The electrode device 330 can include an electrode pad 336, a support frame 337, and a conductor member (not shown) disposed between the electrode pad 336 and the support frame 337. The electrode pad 336 can be formed at least in part with an absorptive material, such as, for example, felt as described above for electrode assemblies 130, 230. The pad 336 can be coupled to the support frame with, for example, ultrasonic welding, thermal coupling, sewing or adhesives.

In some embodiments, the electrode device 330 includes two snap-fit couplings configured to be matingly coupled to an inner surface of an orthosis device, as previously described for other embodiments. The electrode device 330 also includes a magnet member 341 that can help locate and/or align the snap-fit couplings 340 with mating snap-fit couplings on an orthosis device. For example, the orthosis device can have a mating magnetically attracted metallic component disposed between its snap-fit couplings in a similar manner as the electrode device 330. When the electrode device 330 is being placed on the orthosis device, the magnet member 341 will be drawn toward the metallic component, which will in turn align the snap-fit couplings of the electrode device 330 to the mating snap-fit couplings on the orthosis device. Alternatively, instead of the snap-fit couplings, the electrode device 330 and the orthosis can be magnetically coupled.

In alternative embodiments, the electrode device 330 can be coupled to an orthosis device using any of the coupling methods described herein for other embodiments. For example, the electrode device 330 can be coupled to an orthosis device using one or more snap-fit couplings and/or one or more magnetic couplings and/or one or more VELCRO couplings as described herein. Additionally, more than one electrode device 330 can be coupled to an orthosis device.

FIGS. 34-43 illustrate an embodiment of an electrode device 430 that includes two electrodes that are coupled to a single backing, but that are not electrically coupled directly to one another. The electrode device 430 can be used, for example, with a panel (see, e.g., FIGS. 44-46), similar to, for example, panel 288 described above. The electrode device 430 includes a first electrode pad 443, a second electrode pad 445, a first conductor member 447 and a second conductor member 449. The first conductor member 447 and the second conductor member 449 can be formed with, for example, a metallic mesh material. In some embodiments, the first conductor member 447 and/or the second conductor member 449 can be formed with, for example, stainless steel mesh. The first electrode pad 443 and the second electrode pad 445 can be, for example, formed with an absorptive material, such as, for example, felt as described above for electrode assemblies 130, 230. As used herein, the first electrode pad 443 and the first conductor member 447 can also be collectively referred to as a first electrode, and the second electrode pad 445 and the second conductor member 449 can also be collectively referred to as a second electrode.

Figure 35:
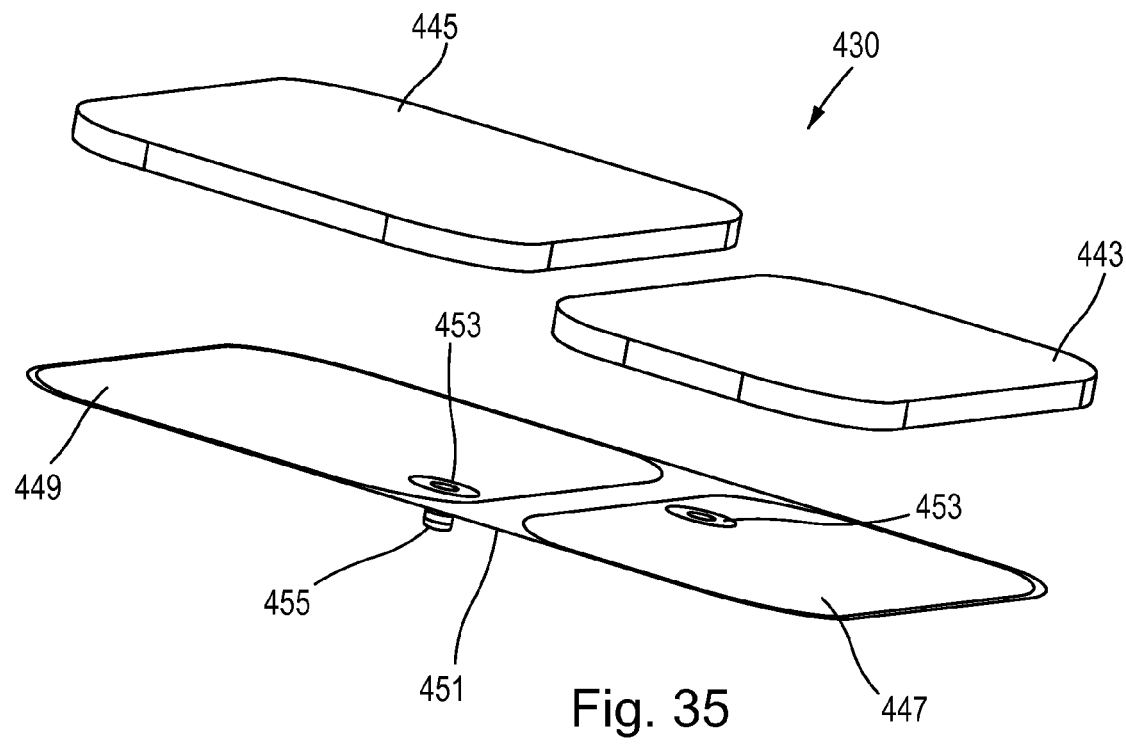
FIG. 35 is a partial exploded view of the electrode assembly of FIG. 34.
Figure 36:
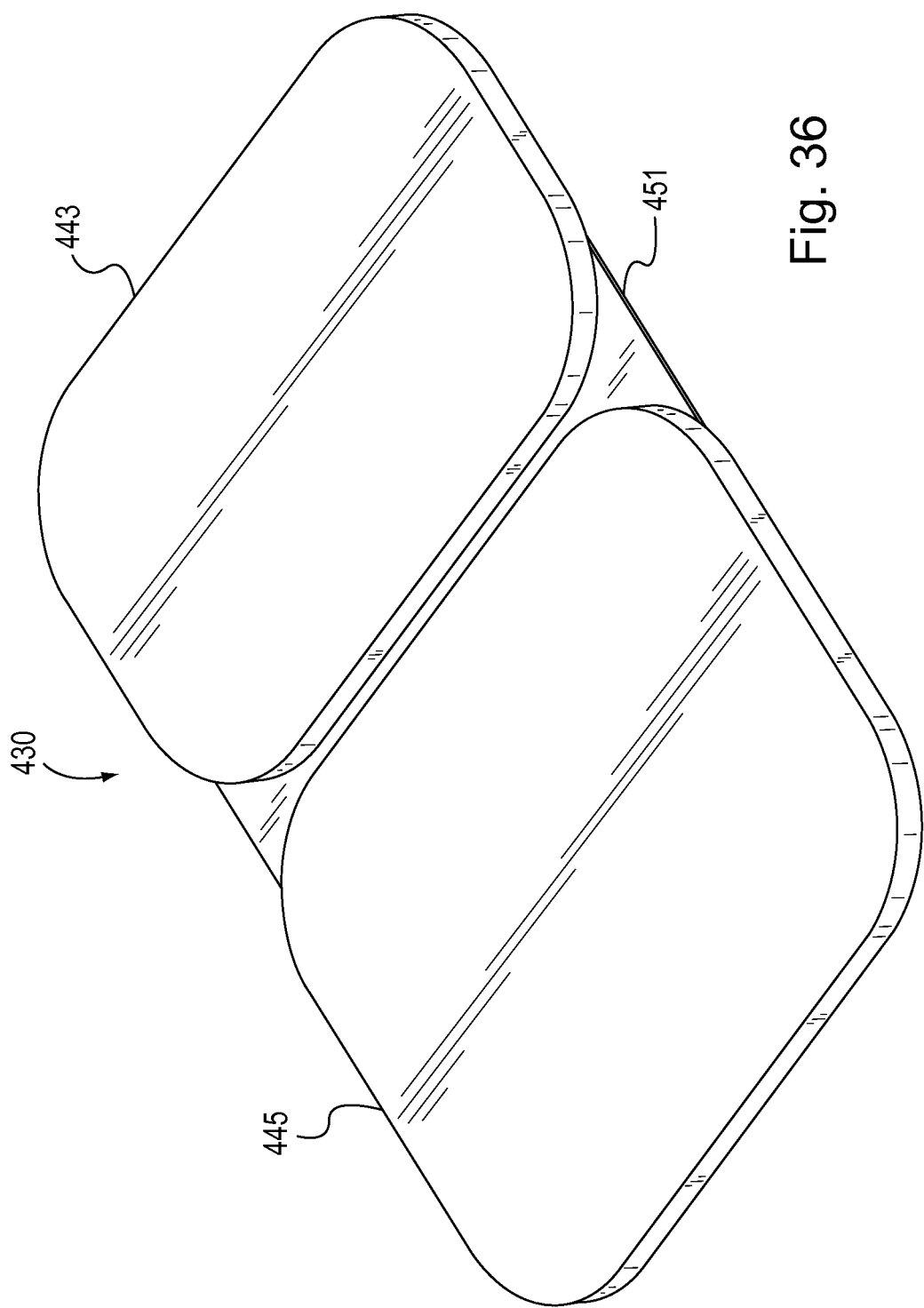
FIG. 36 is a top perspective view of the electrode assembly of FIG. 35.
Figure 37:
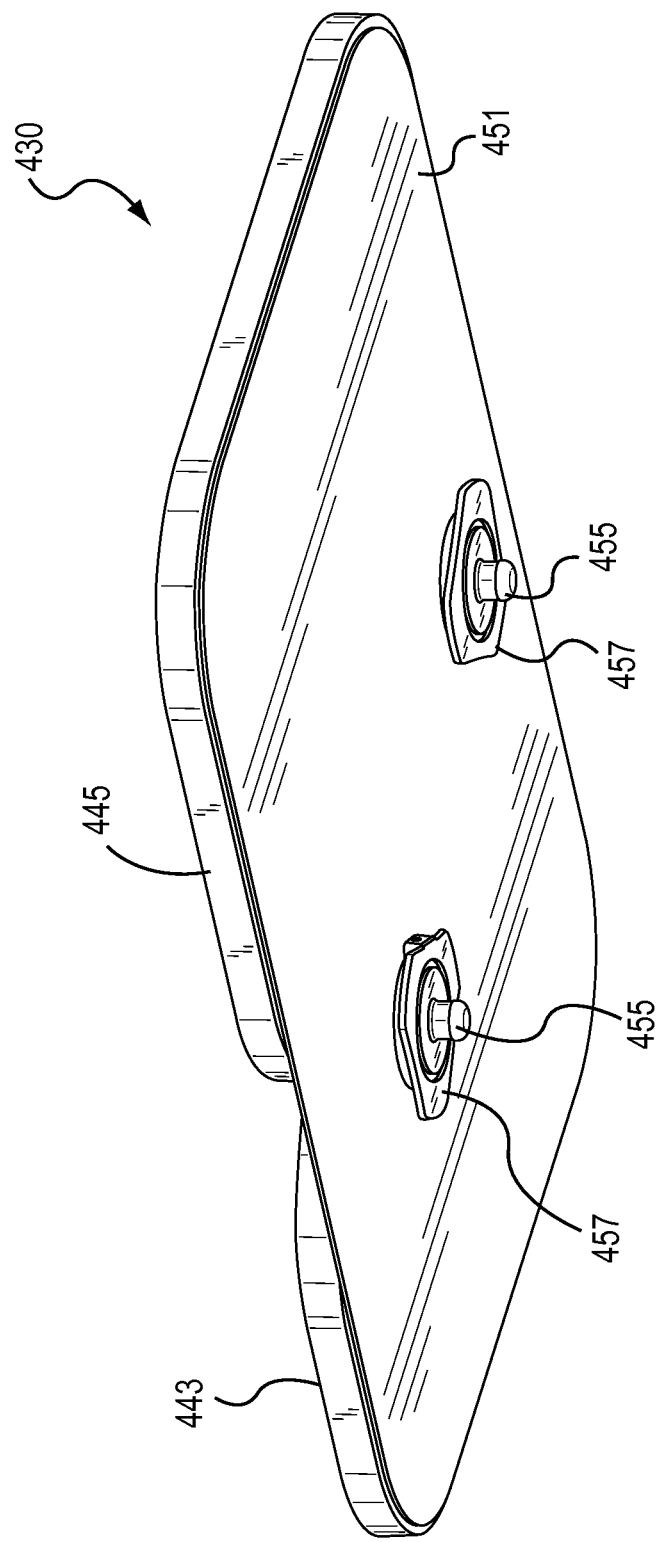
FIG. 37 is a bottom perspective view of the electrode assembly of FIG. 35.
Figure 38:
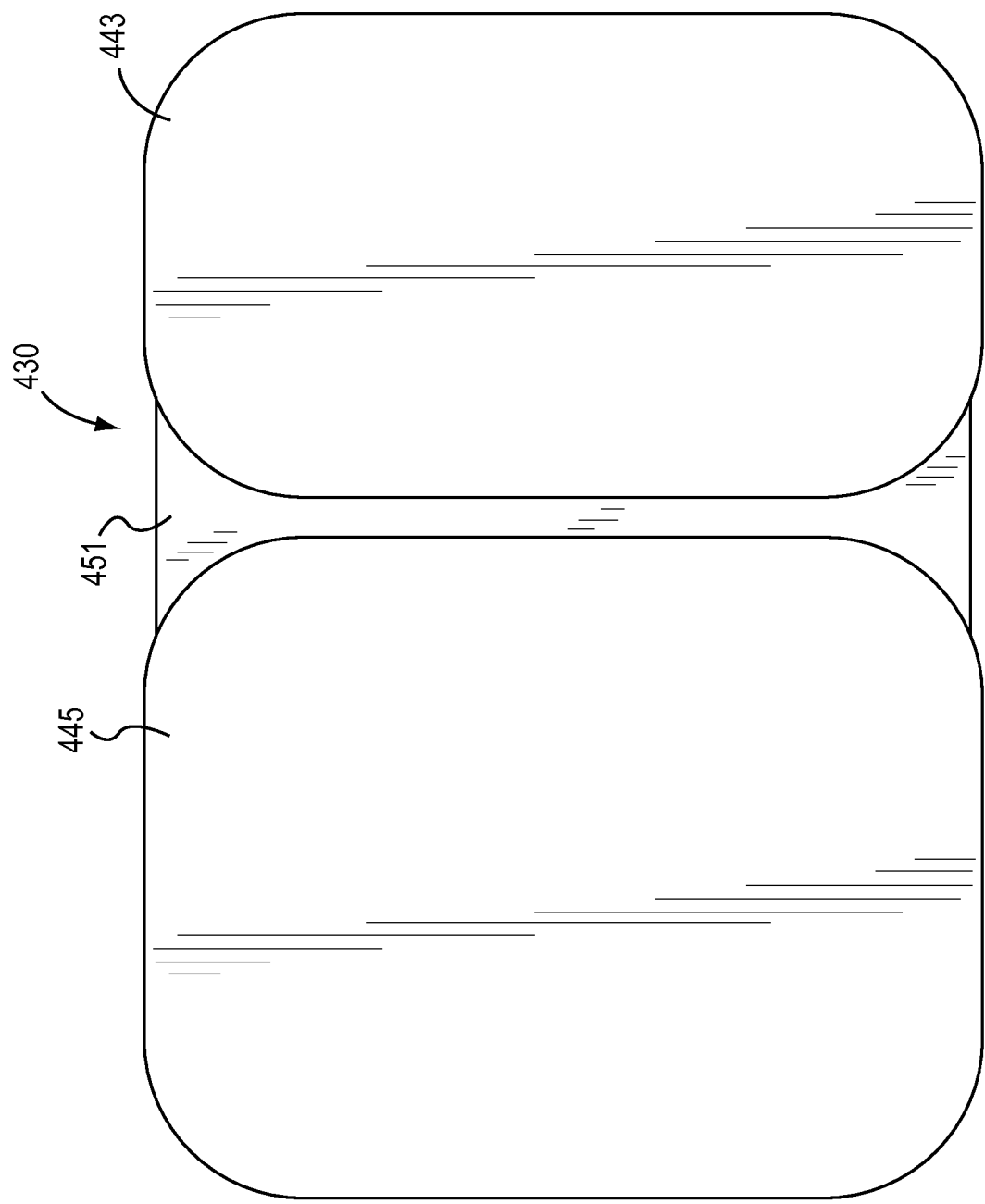
FIG. 38 is a top view of the electrode assembly of FIG. 35.
Figure 39:
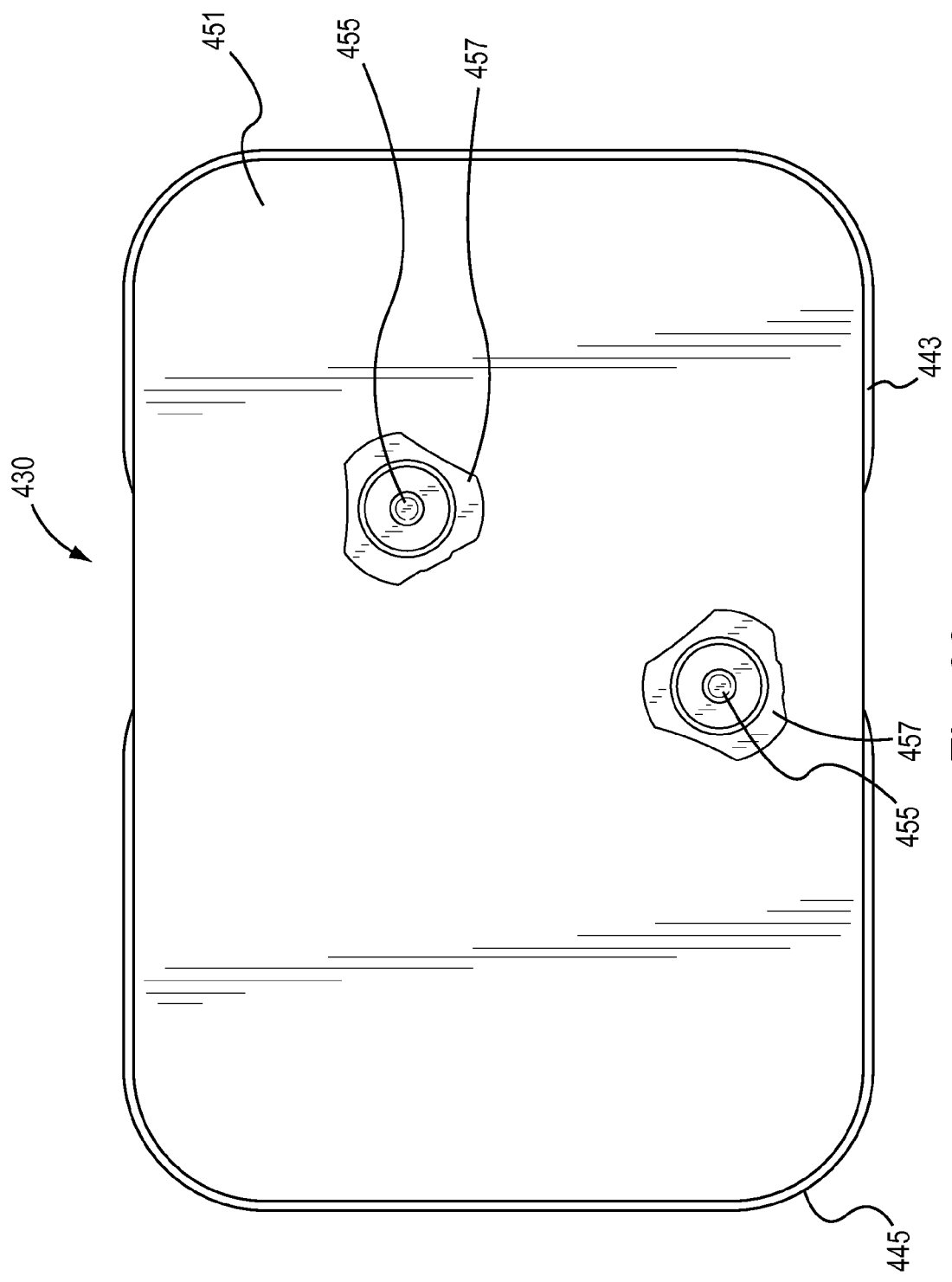
FIG. 39 is a bottom view of the electrode assembly of FIG. 35.
Figure 40:
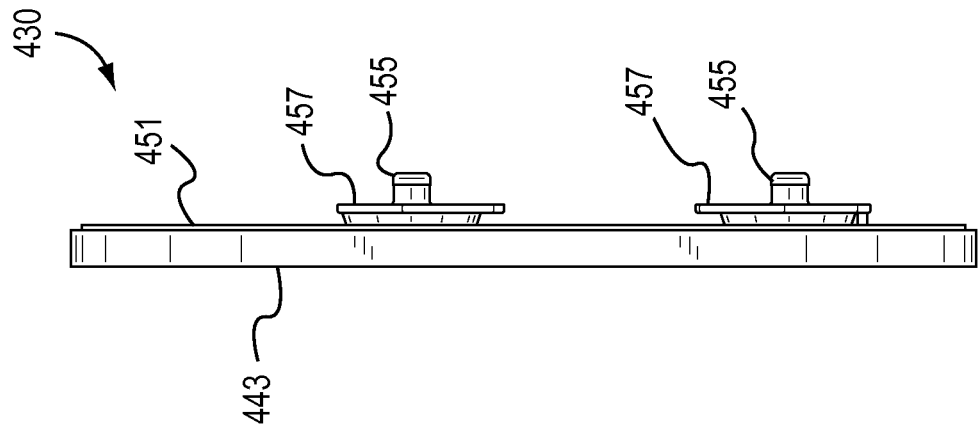
FIG. 40 is a right side view of the electrode assembly of FIG. 35.
Figure 41:
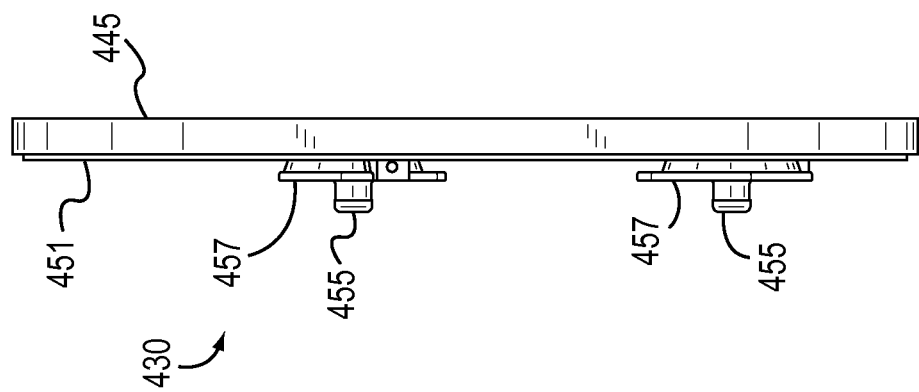
FIG. 41 is a left side view of the electrode assembly of FIG. 35.

The first conductor member 447 and the second conductor member 449 are each coupled to a base 451 as shown in FIG. 35. An electrical snap stud member 453 is inserted through holes 461 in each of the first conductor member 447 and the second conductor member 449, and corresponding holes 463 in the base 451 (see e.g., the exploded view of FIG. 34). The electrical snap stud members 453 pass through an opening in spacers 457 and are inserted into mating snap post members 455. The spacers 457 can be used to fill a cavity that may be present between the mating snap connectors inside a functional electrical stimulation (FES) orthosis device and enable the electrode device 430 to snap directly to the orthosis. The snap post members 455 can be used to mechanically couple the electrode device 430 to the orthosis and can also be used to conduct electrical current from the orthosis to the first conductor member 447 and the second conductor member 449.

The first electrode pad 443 and the second electrode pad 445 can each be coupled to the base 451 with the first and second conductor members 447 and 449 disposed between the base 451 and the electrode pads 443 and 445. The first electrode pad 443 and the second electrode pad 445 can each be coupled to the base 451 with, for example, hook and pile fasteners, an adhesive, or other suitable coupling method. The location of the first and second conductor members 447 and 449 below the first and second electrode pads 443 and 445, respectively, allows for the electrical stimulation during a FES treatment to be distributed evenly across the first and second electrode pads 443 and 445 and to the target treatment site as discussed above for previous embodiments.

Figure 44:
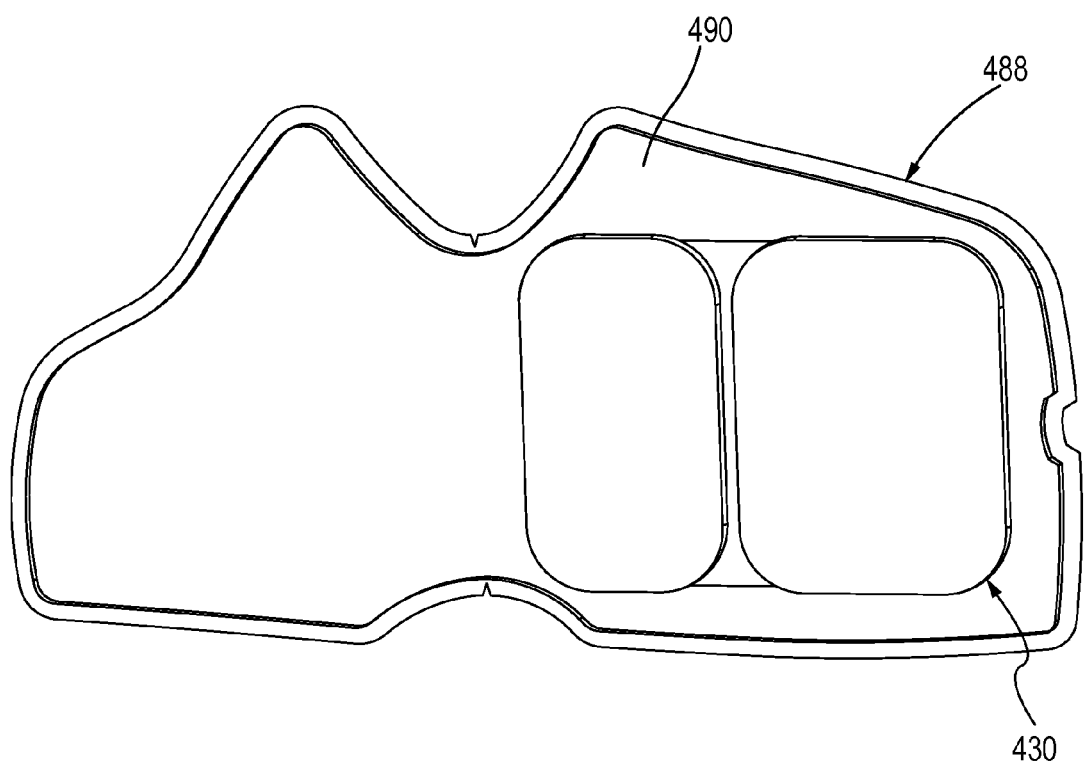
FIG. 44 is a front perspective view of the electrode assembly of FIG. 35 and a panel member according to an embodiment.
Figure 45:
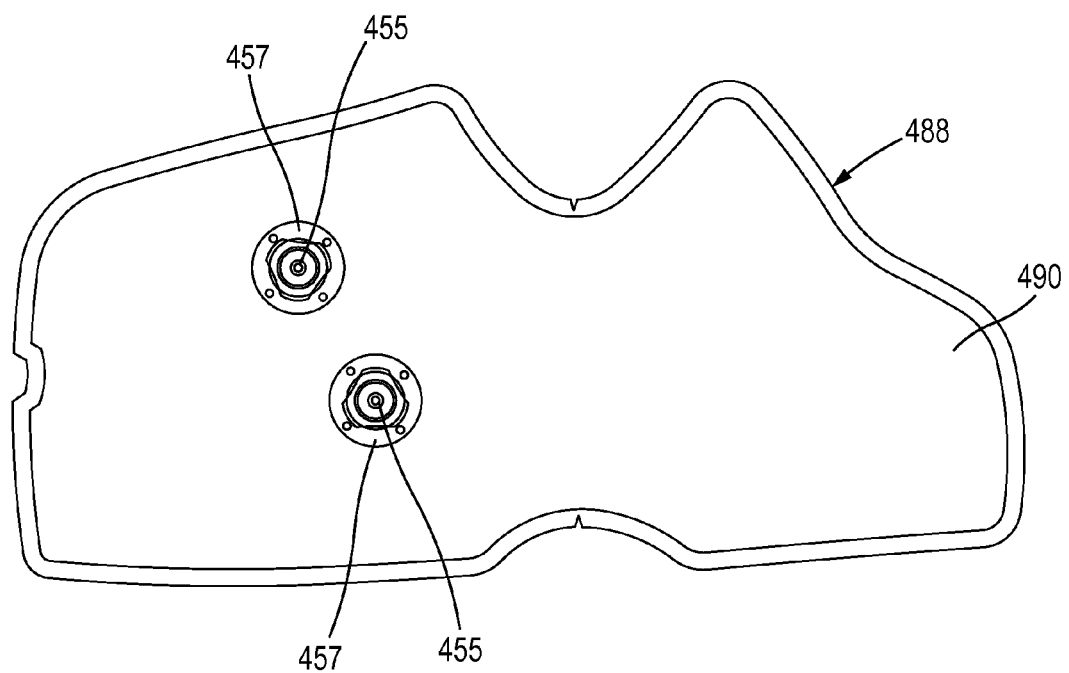
FIG. 45 is a front or inside view of the panel member of FIG. 44.
Figure 46:
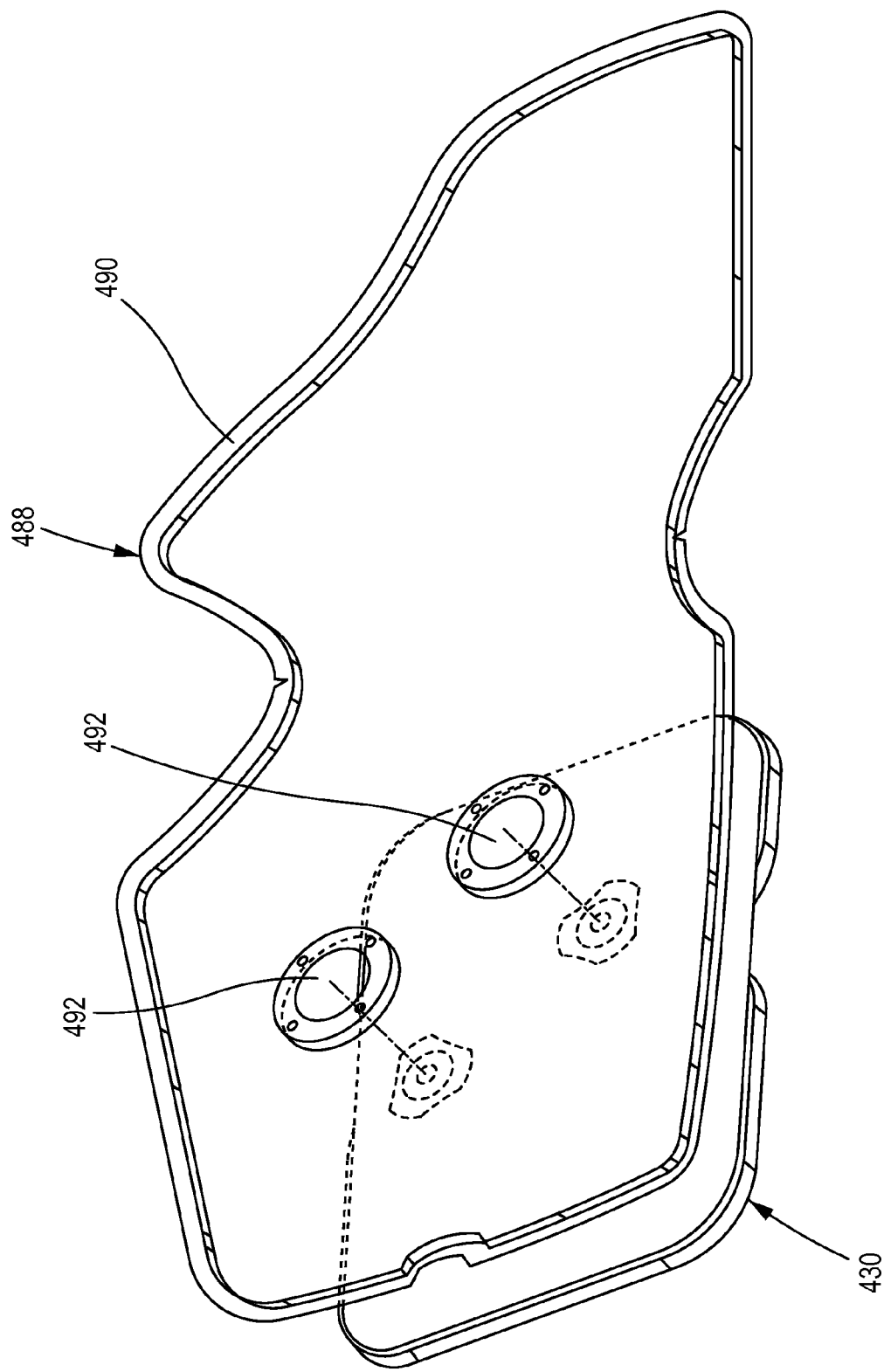
FIG. 46 is an exploded view of the panel member of FIG. 45 and electrode assembly of FIG. 35 with the panel member shown transparent.
Figure 47:
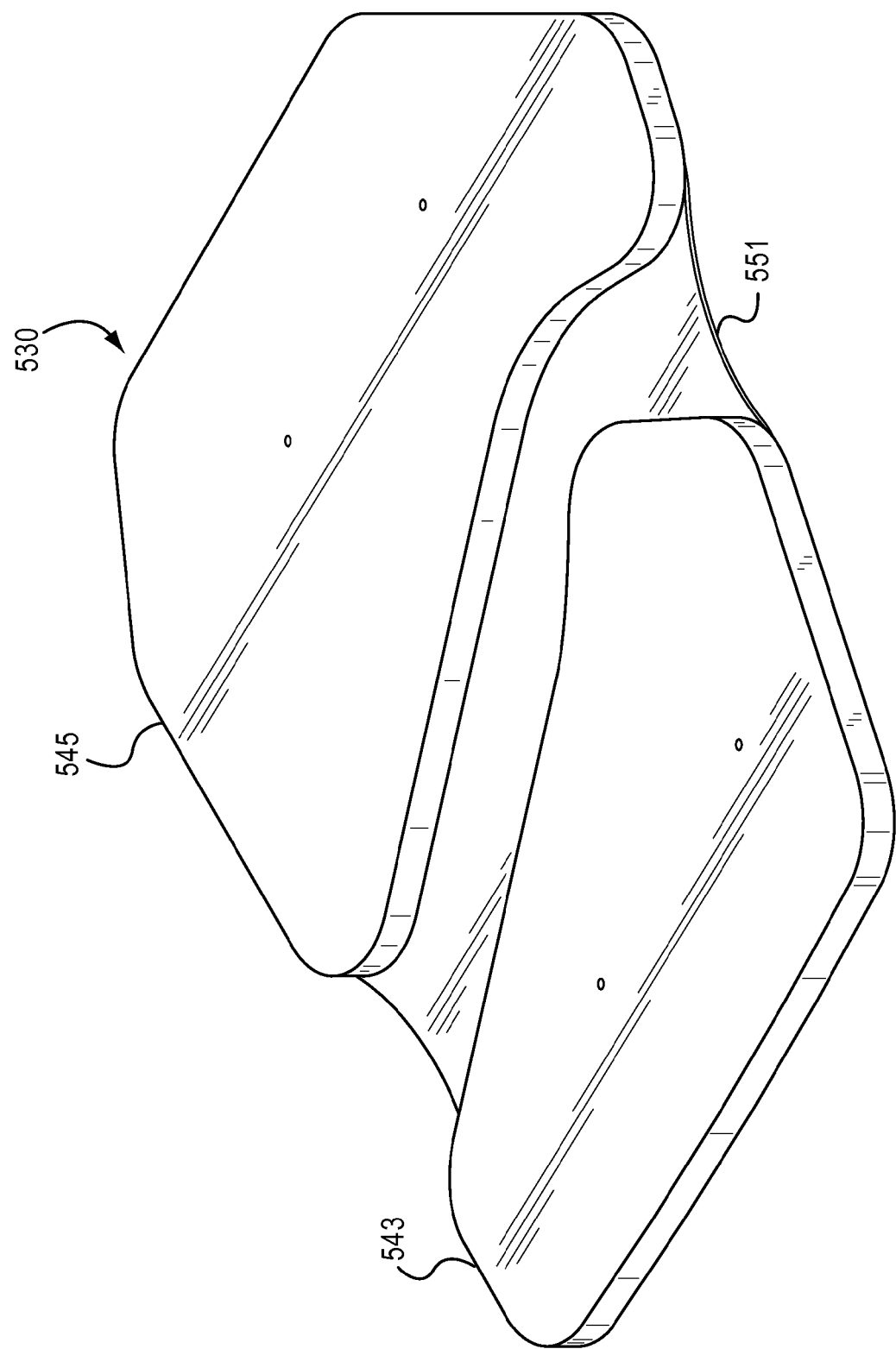
FIG. 47 is a front perspective view of an electrode assembly according to an embodiment.

As discussed above, the electrode device 430 can optionally be coupled to a panel 488 as shown in FIGS. 44-46. The panel 488 includes a panel member 490 that defines two openings 492 (see, FIG. 46). The panel member 490 can be formed with a flexible material that can conform to the inner surface of an orthosis. The panel member 490 can be formed, for example, with a fabric, cloth, felt, velvet, or other suitable material. Each of the openings 492 can receive an electrical snap stud member 455 of the electrode device 430.

The panel 488 can be releasably coupled to an orthosis device (not shown) as described above for previous embodiments. For example, the electrode assembly 430 can be coupled to the panel 488 and the electrical snap stud members 455 (extending through the openings 492) can be coupled to a mating snap-fit coupler on the orthosis device. In some embodiments, the panel 488 can also include a coupling member (not shown), such as a VELCRO attachment member configured to be coupled to a mating VELCRO attachment (not shown) on the inner surface of the orthosis device. In some embodiments, additional snap-fit couplings and/or magnetic couplings can be used to couple the panel 488 to the orthosis device.

FIGS. 47-58(e) illustrate another embodiment of an electrode device that includes two electrodes (e.g., a pad and conductor member) that are coupled to a single backing, but that are not electrically coupled directly to one another. The electrode device 530 includes a first electrode pad 543, a second electrode pad 545, a first conductor member 547 and a second conductor member 549 (see e.g., FIG. 48). The first conductor member 547 and the second conductor member 549 can be formed with, for example, a metallic mesh material, such as stainless steel. The first electrode pad 543 and the second electrode pad 545 can be, for example, formed with an absorptive material, such as, for example, felt as described for previous embodiments. As used herein, the first electrode pad 543 and the first conductor member 547 can also collectively be referred to as a first electrode, and the second electrode pad 545 and the second conductor member 549 can also collectively be referred to as a second electrode.

Figure 48:
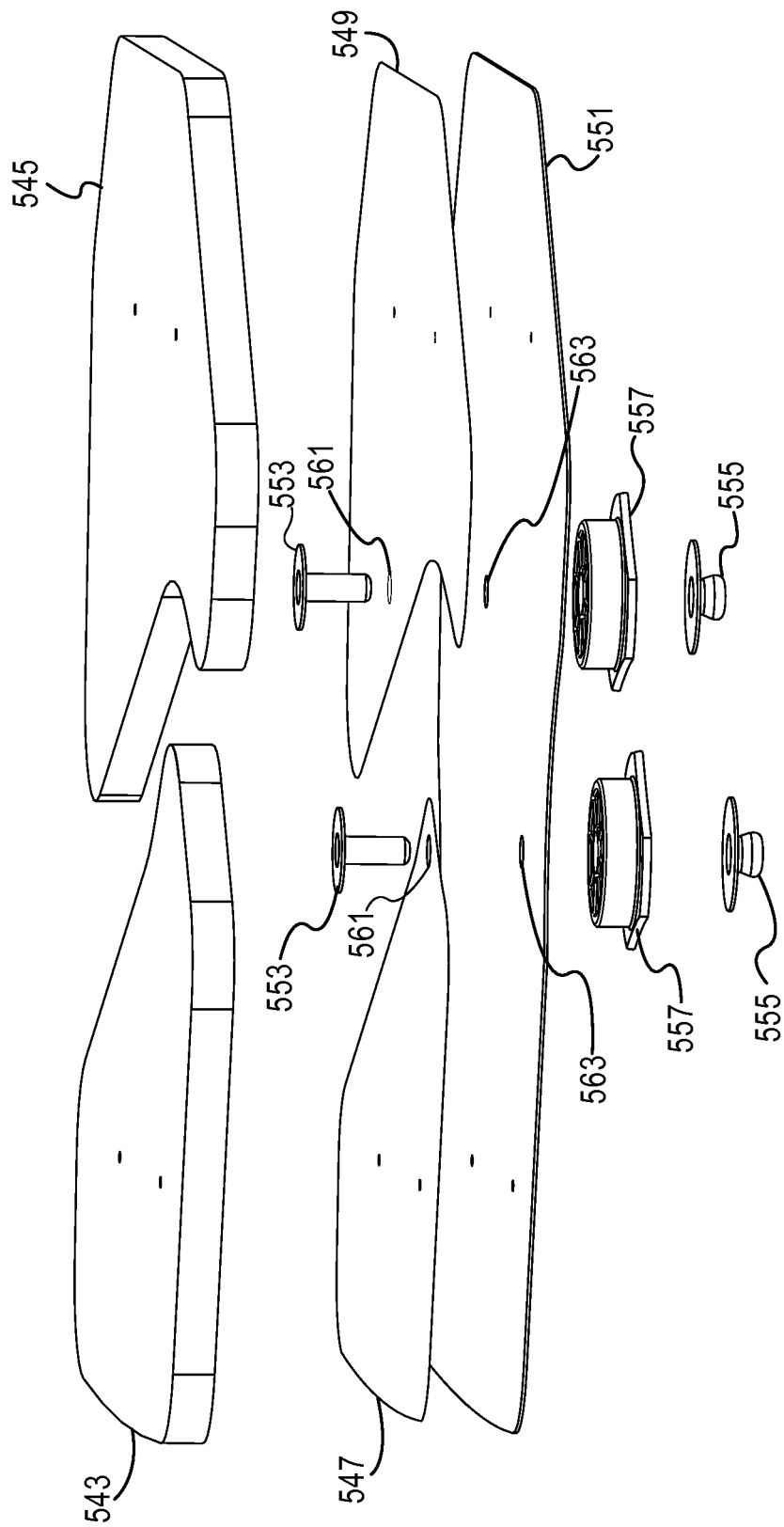
FIG. 48 is an exploded view of the electrode assembly of FIG. 47.
Figure 49:
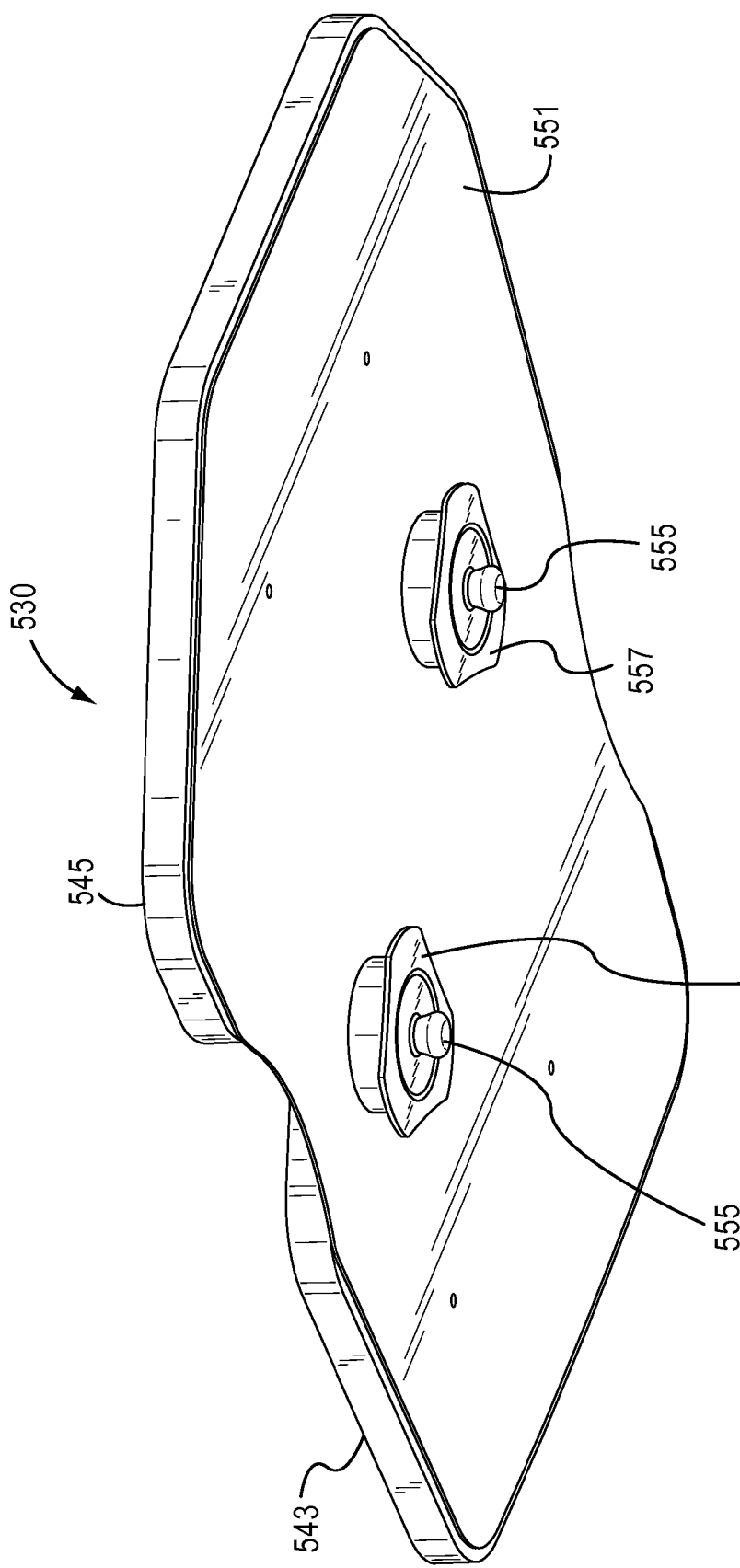
FIG. 49 is a bottom perspective view of the electrode assembly of FIG. 47.
Figure 50:
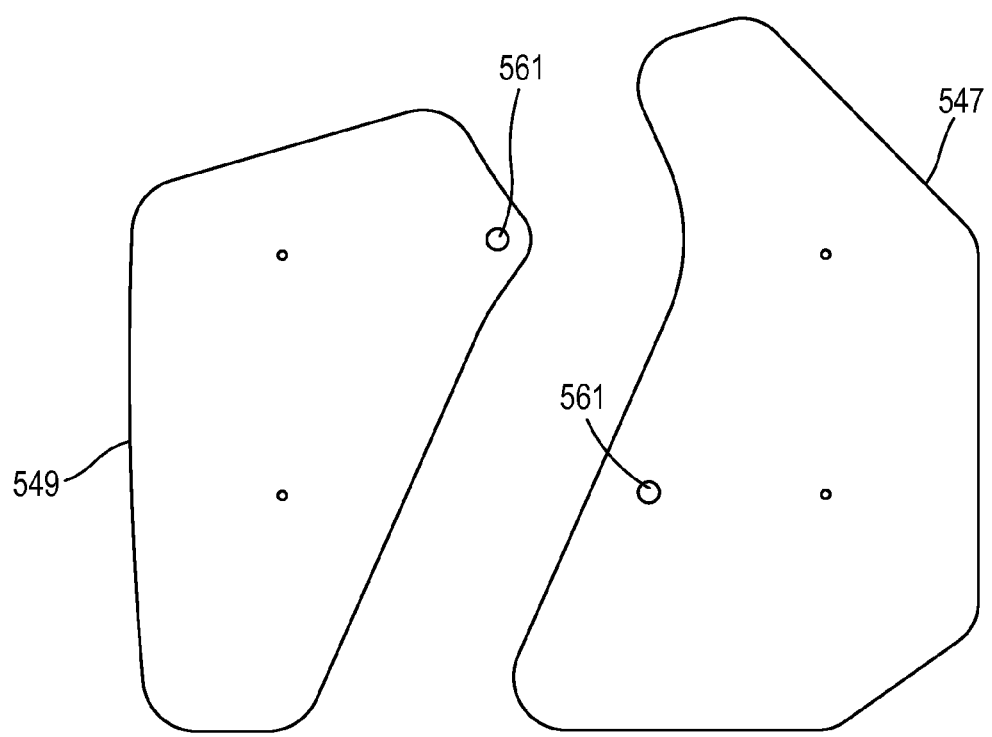
FIG. 50 is a top view of two conductor members of the electrode assembly of FIG. 47.
Figure 51:
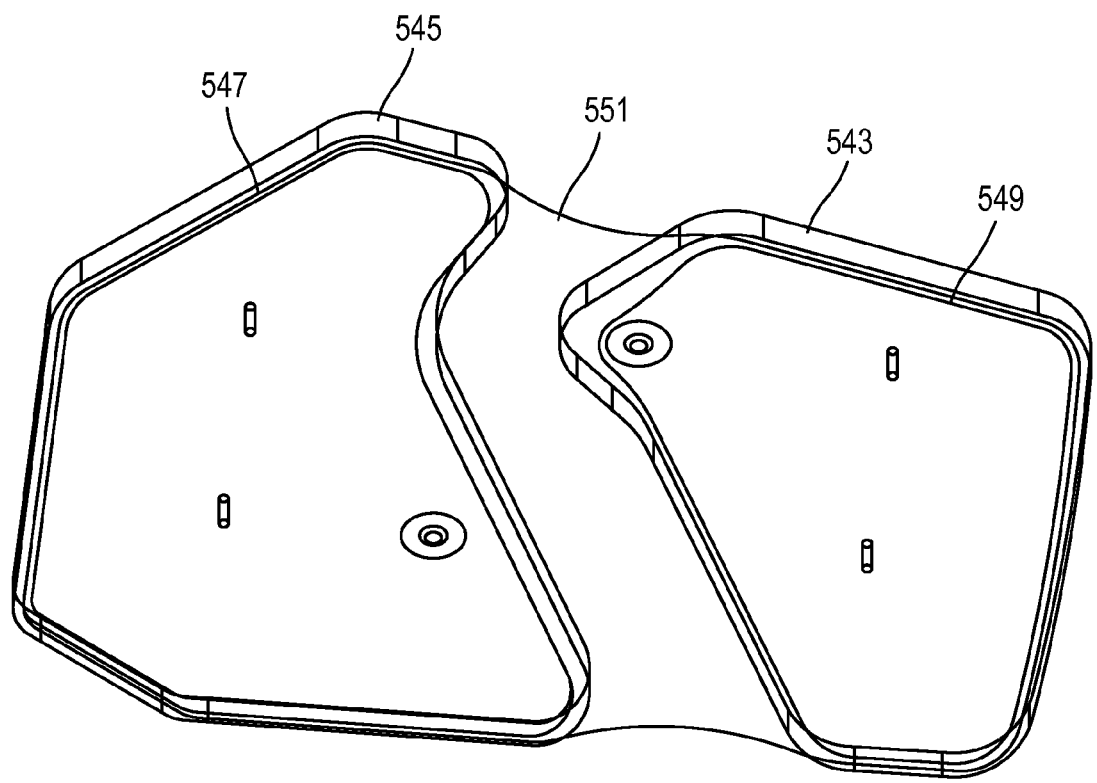
FIG. 51 is a front perspective view of the electrode assembly of FIG. 47 shown partially transparent.
Figure 52:
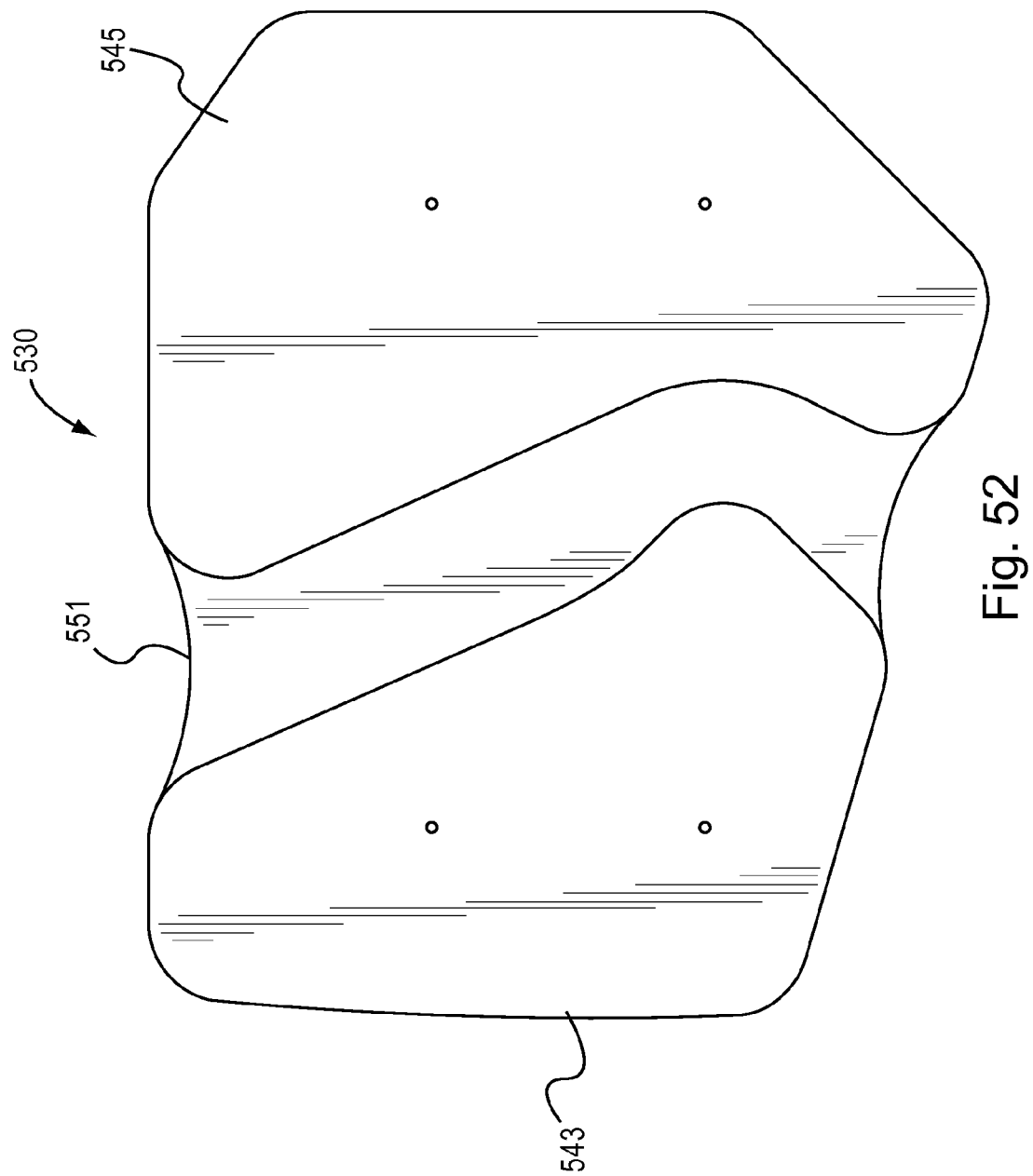
FIG. 52 is a top view of the electrode assembly of FIG. 47.
Figure 53:
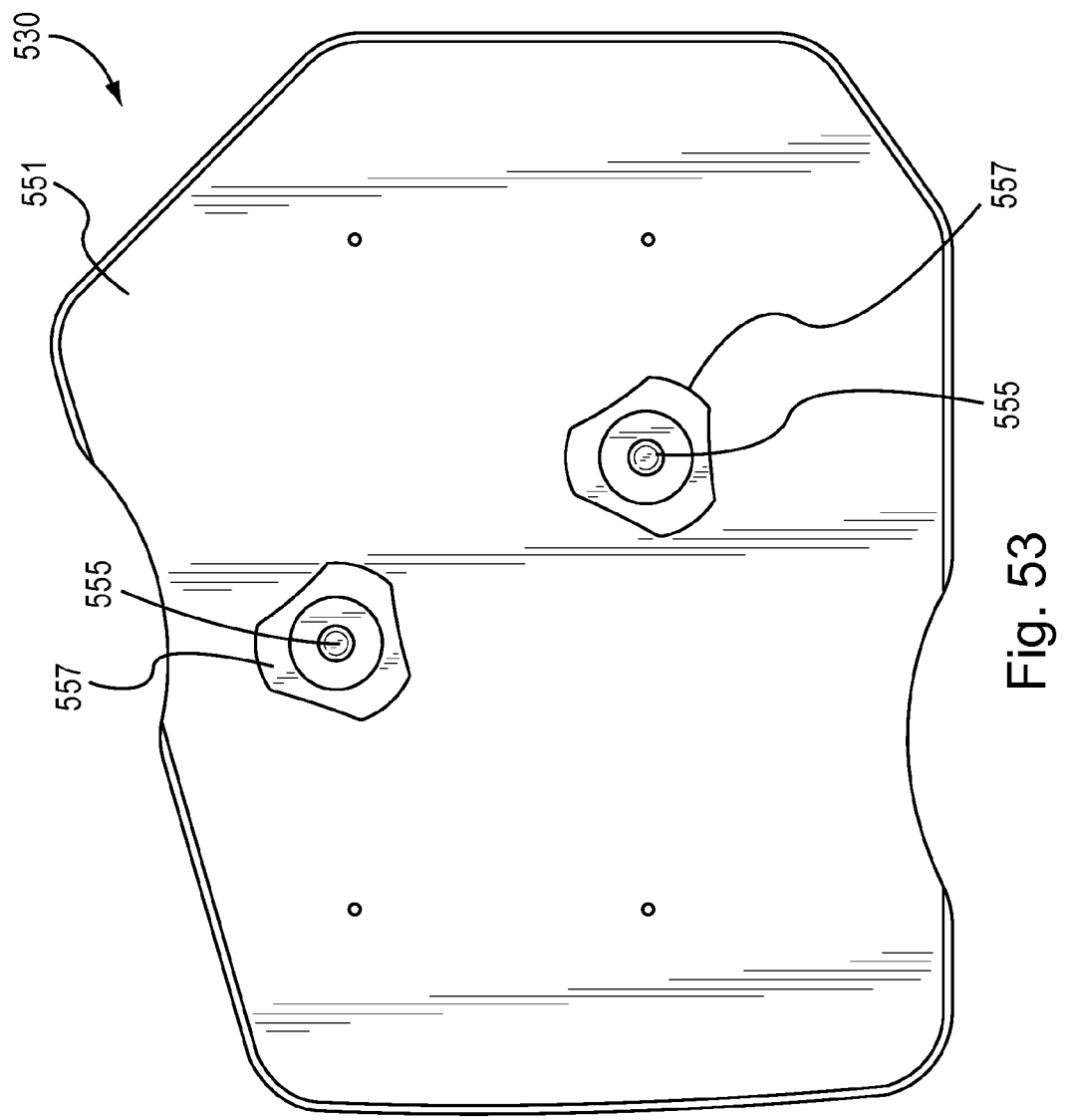
FIG. 53 is a bottom view of the electrode assembly of FIG. 47.
Figure 54:
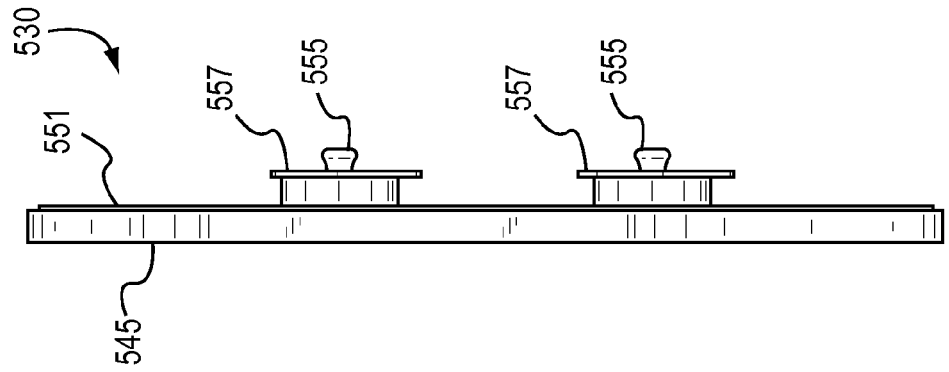
FIG. 54 is a right side view of the electrode assembly of FIG. 47.
Figure 55:
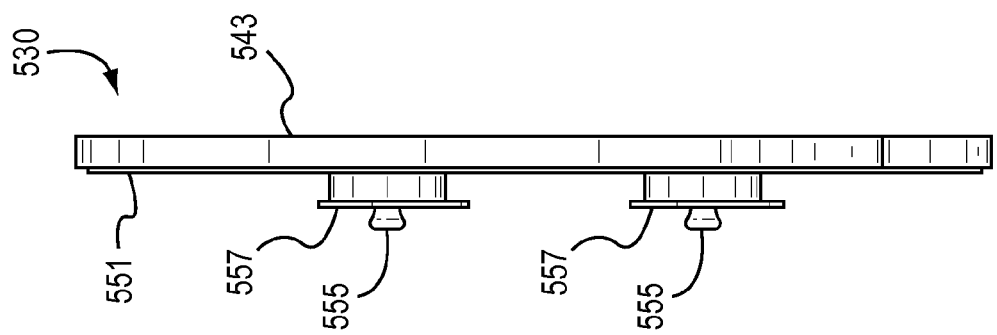
FIG. 55 is a left side view of the electrode assembly of FIG. 47.
Figure 56:
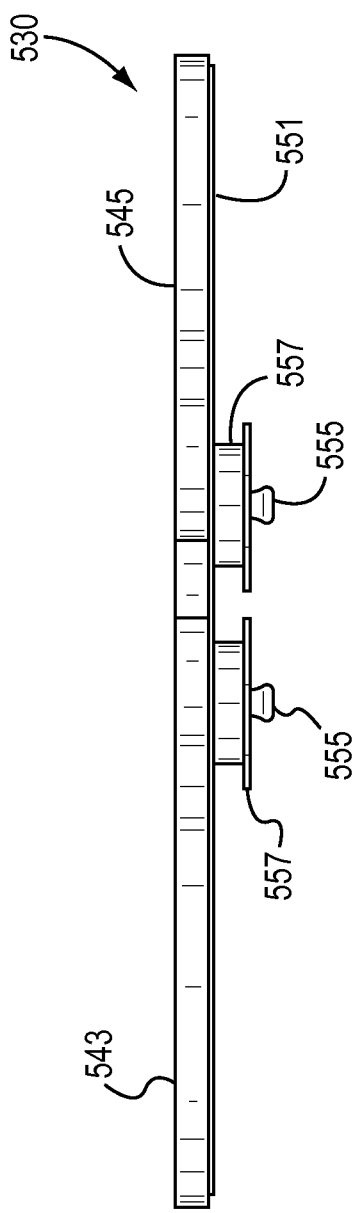
FIG. 56 is a front end view of the electrode assembly of FIG. 47.
Figure 57:
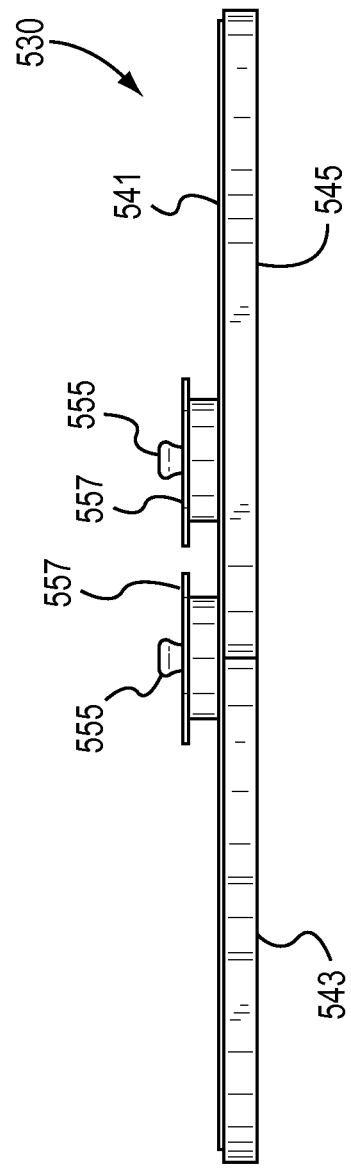
FIG. 57 is a rear end view of the electrode assembly of FIG. 47.

The first conductor member 547 and the second conductor member 549 are each coupled to a base 551 as shown in for example, FIGS. 48 and 51. An electrical snap stud member 553 is inserted through holes 561 (see e.g., FIG. 50) in each of the first conductor member 547 and the second conductor member 549 and corresponding holes 563 in the base 551 (see e.g., FIG. 48). The electrical snap stud members 553 pass through an opening in spacers 557 and are inserted into mating snap post members 555. As described above for electrode device 430, the spacers 557 can be used to fill a cavity that may be present between the mating snap connectors inside a functional electrical stimulation orthosis and enable the electrode assembly 530 to snap directly to the orthosis. The snap post members 555 can be used to mechanically couple the electrode assembly 530 to the orthosis and can also be used to conduct electrical current from the orthosis to the first conductor member 547 and the second conductor member 549.

The first electrode pad 543 and the second electrode pad 545 can each be coupled to the base 551 with the conductor members 547 and 549 disposed between the base 551 and the first and second electrode pads 543 and 545 (see e.g., FIG. 51 which shows the first and second electrode pads 543 and 545 partially transparent). The location of the first and second conductor members 547 and 549 below the first and second electrode pads 543 and 545, respectively, allows for the electrical stimulation during a FES treatment to be distributed evenly across the first and second electrode pads 543 and 545 and to the target treatment site as discussed above for previous embodiments.

The electrode device 530 can optionally be coupled to a panel (not shown), such as, for example, panel 488, as described above for electrode device 430. The panel can be releasably coupled to an orthosis device (not shown) as described above for previous embodiments. The electrode device 530 can also be coupled directly to an orthosis device. For example, the electrical snap stud members 555 extending from a back side of the electrode device 530 (see e.g., FIG. 49) can be coupled to a mating snap-fit coupler on the orthosis device.

Figures 58A, 58B, 58C:
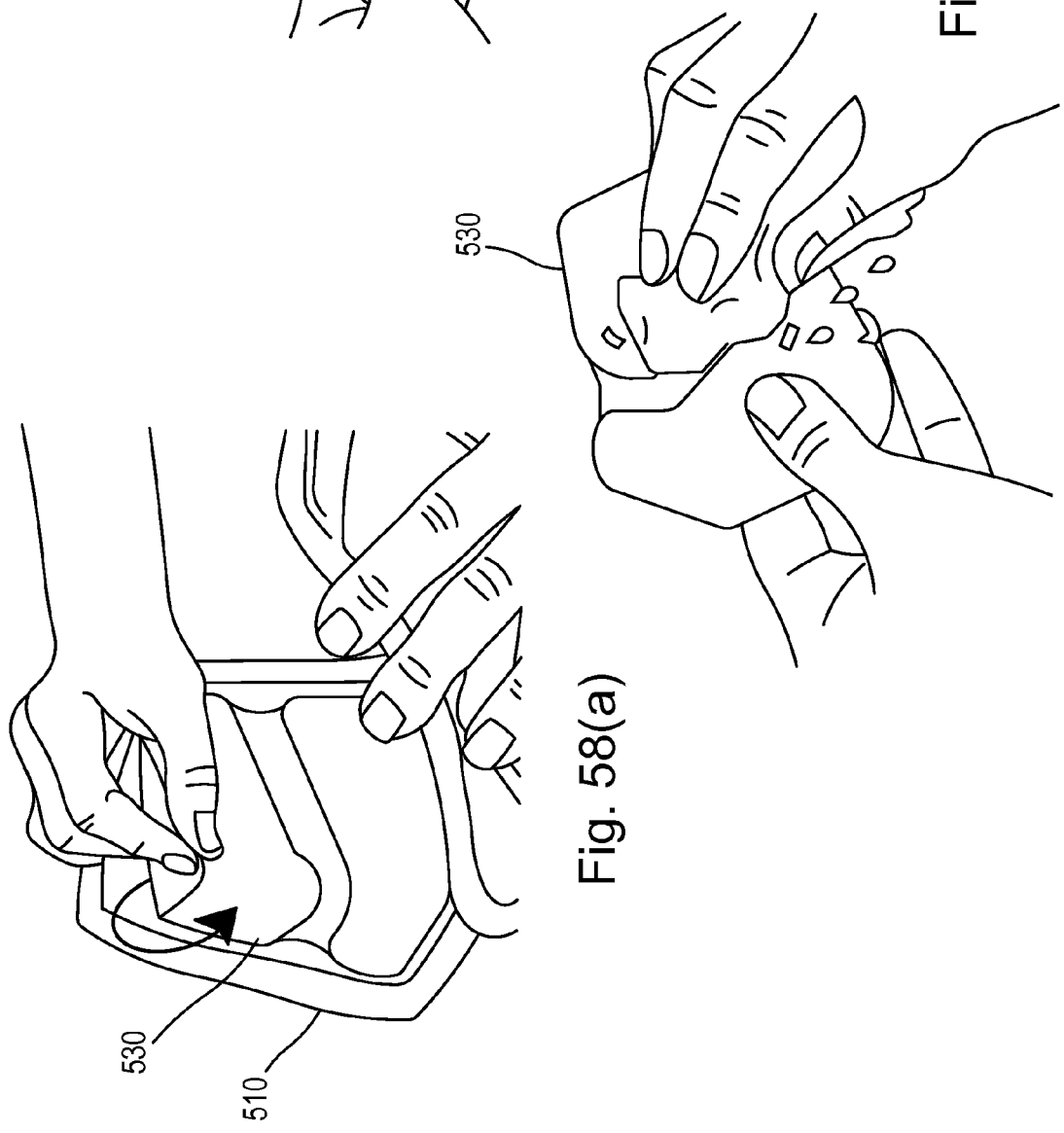
FIG. 58(a) through 58(e) are each an illustration showing a step in a method of preparing an electrode assembly for use with an orthosis device.
Figure 58E:
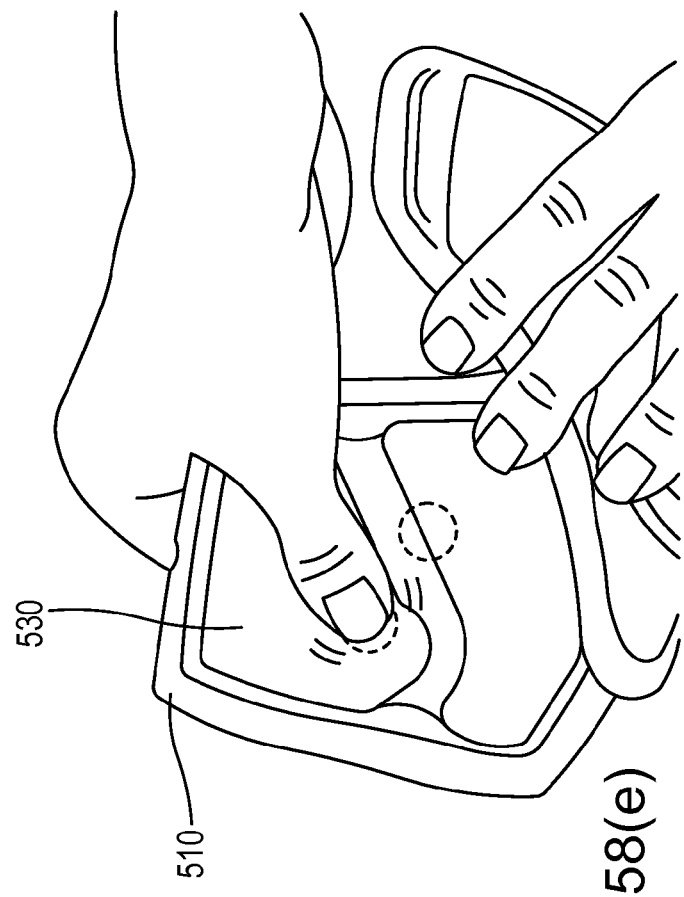
Figure 58D:
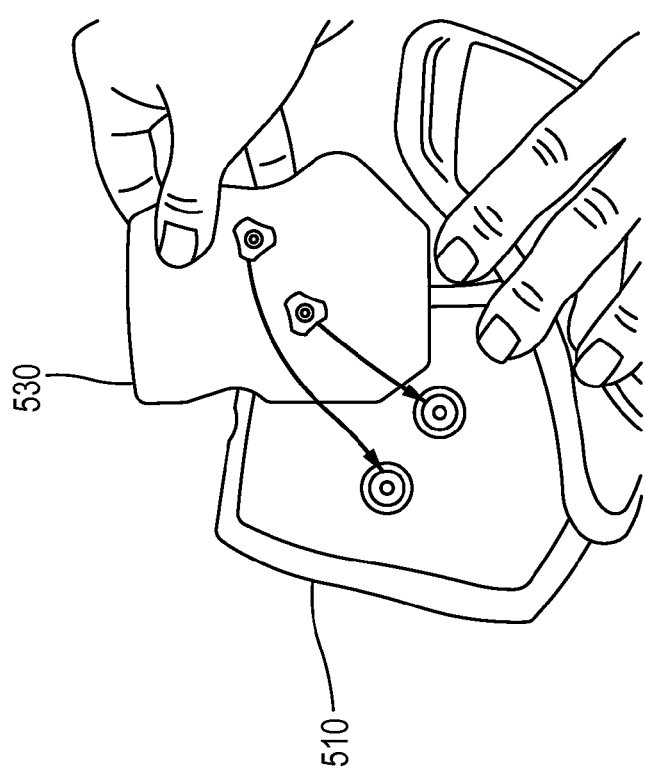

FIGS. 58(*a*)-58(*e*) illustrate one example of preparing an electrode device 530 for use with an orthosis device 510 to be used for electrical stimulation during a FES treatment. As shown in FIG. 58(*a*), with the orthosis system turned off, the electrode device 530 can be removed from the orthosis device 510 by detaching the snap stud members 555 from the orthosis device 510. The electrode device 530 can then be wet with water as shown in FIG. 58(*b*). Excess water can be removed from the electrode device 530 using a cloth or, for example, a paper towel as shown in FIG. 58(*c*). To place the electrode device 530 back onto the orthosis device 510, the snap stud members 555 on the electrode device 530 can be aligned with mating coupling holes on the orthosis device 510 (as shown in FIG. 58(*d*)), and the electrode device 530 can be pressed firmly to snap the snap stud members 555 thereto (as shown in FIG. 46(*e*)). In some embodiments, the snap stud members 555 are color coded to align with color coded rings or markings around the mating openings on the orthosis device 510.

The electrode devices 330, 430 and 530 described above are examples of large electrode devices that can be used in conjunction with a surface neuroprosthesis device or orthosis for functional electrical stimulation (FES) and/or neuromuscular electrical stimulation (NMES) of a targeted body tissue (e.g., muscle, ligament), such as an impaired limb. The electrode devices 330, 430 and 530 can have various other shapes and sizes and can be used, for example, within an orthosis of a foot drop system used in the treatment of drop foot. The electrode devices 330, 430 and 530 can be used for example, in an orthosis device described in the '149 application incorporated by reference herein. The electrode devices 330, 430 and 530 can include one or more conductor members and one or more electrode devices 330, 430 and 530 can be coupled to an orthosis.

The large electrode device (330, 430, 530) is "large" in the sense that it is not narrowly focused for providing stimulation to a narrowly defined area. The size and shape of the large electrode device allows the large electrode device to be used to stimulate a larger group of muscles and produce a more comfortable stimulation. For example, a large electrode device can be configured to provide electrical stimulation to a substantial portion of a peroneal nerve when used, for example, to treat drop foot.

In one example use of a large electrode device with an orthosis configured to be coupled to a patient's upper leg as disclosed in the '149 application incorporated by reference herein, the resulting physiological effects achieved during the test include the following:

(1) satisfactory, neutral dorsiflexion of 5-10 degrees during gait was achieved with 87% of the test subjects;

(2) maintaining the desired dorsiflexion during gait after a conditioning period of 3 weeks and without causing muscle fatigue while using the orthosis/large electrode for up to 14 hours a day; and (3) consistency of motor response.

The large electrode device is able to produce stimulation sufficient to treat a larger population of patients with a single sized device placed in substantially the same location for each patient. For example, in some embodiments, a large electrode device can have a size and shape configured to be used by 85% of patients. The large electrode devices (330, 430, 530) can be configured to fit a left side, a right side, and/or both a left side and a right side orthosis, such as an orthosis used in the treatment of drop foot that is placed on the patient's right or left leg.

A large electrode device (e.g., 330, 430, 530) can provide a quick and reproducible means of positioning electrodes inside an orthosis so as to decrease the time of electrode set-up and/or eliminate clinicians having to adjust the electrode position to achieve optimal stimulation results. A large electrode device can also decrease training time of the customer and eliminate the need to mark the precise position of electrodes with a marking pen on the user's body. While smaller electrodes can be effectively placed in one of many possible optimal positions, the use of the large electrode eliminates the need for more precise placement of the electrode and orthosis. The use of the large electrodes makes the orthosis "one size fits all" or "one size fits most."

In some embodiments, a large electrode device is placed at a location on the inside of the orthosis without regard to the particular patient for whom the device is being configured. In some embodiments, multiple large electrode devices are placed at a location on the inside of the orthosis without regard to the particular patient. In some embodiments, the electrode devices cover substantially all of the interior area of the orthosis to which they are coupled. For example, in some embodiments, the electrode devices span the interior area of the orthosis device other than, for example, the gap between the electrode devices and the gap, if any, between the outer edge of the electrode devices and the edge of the orthosis.

The large electrode devices (e.g., 330, 430, 530), can have varied sizes and shapes and can be positioned on an orthosis to achieve various desired treatment results. In some embodiments, a large electrode device can include, for example, a first medial electrode (e.g., collectively the pad and conductor members) and a second lateral electrode (e.g., collectively the pad and conductor members) having sizes as shown in Table 1 below. The medial electrode can be positioned on an orthosis, for example, at a distance from the orthosis midline in the range of 0 to 0.5 cm. In some embodiments, the medial electrode and the lateral electrode can be coupled to a base of the large electrode at a non-zero distance from each other (e.g., a gap between the medial and lateral electrodes) of between 1.5 mm and 2.5 mm. For example, in some embodiments, the gap between the electrodes is 1.5 mm, 2.0 mm, or 2.5 mm. It should be understood that these are merely example sizes and positions and that the large electrode devices can have other combinations of widths and lengths and other shapes. For example, in some embodiments, a large electrode device (e.g., 430, 530) can include one or more electrodes (e.g., collectively the pad and conductor members) with a width between 30 mm and 75 mm and a length of about 95 mm. For example, a large electrode can have a width of 30 mm, 35 mm, 40 mm, 45 mm, 50 mm, 55 mm, 60 mm, 65 mm, 70 mm, or 75 mm and a length of, for example, 95 mm. The electrodes can also be positioned at different distances apart from each other and at different locations on an orthosis.

TABLE 1

| Medial electrode size width × length (in mm.) | Gap between medial and lateral electrode (in cm.) | Lateral electrode size width × length (in mm.) |
|---|---|---|
| 55 × 95 | 1.5 | 40 × 95 |
| 55 × 95 | 2.5 | 40 × 95 |
| 55 × 95 | 1.5 | 50 × 95 |
| 55 × 95 | 2.0 | 45 × 95 |

Conclusion

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. The specific configurations of the various components can also be varied. For example, the size and specific shape of the various components can be different than the embodiments shown, while still providing the functions as described herein.

In addition, it should be understood that the electrode kits and electrode assemblies described herein can be used in a variety of different types of orthosis or surface neuroprostheses devices not necessarily described herein. In addition, the devices and methods described herein can be used for a variety of different types of functional electrical stimulation treatments in a variety of different locations on a patient's body.

What is claimed is:

1. An apparatus, comprising:
an electrode base;
a first conductor member coupled to the electrode base;
a second conductor member coupled to the electrode base;
a first pad coupled to the electrode base such that the first conductor member is disposed between the electrode base and the first pad, a portion of the first pad configured to contact a skin surface; and
a second pad coupled to the electrode base such that the second conductor member is disposed between the electrode base and the second pad, a portion of the second pad configured to contact the skin surface,
the electrode base being releasably couplable to an orthosis such that the first conductor member and the second conductor member are each electrically coupled to the orthosis and not electrically coupled to each other.

2. The apparatus of claim 1, wherein the first pad has a width between 30 mm and 75 mm and a length of about 95 mm, and the second pad has a width between 30 mm and 75 mm and a length of about 95 mm.

3. The apparatus of claim 1, wherein the first pad and second pad are each coupled to the electrode base such that there is a gap between the first pad and the second pad.

4. The apparatus of claim 1, wherein the first pad and second pad are each coupled to the electrode base such that there is a non-zero distance between the first pad and the second pad of between 1.5 mm and 2.5 mm.

5. The apparatus of claim 1, further comprising:
a panel member configured to be coupled to the orthosis between the electrode base and the orthosis.

6. The apparatus of claim 1, wherein the first pad has a substantially rectangular shape and the second pad has a substantially rectangular shape.

7. The apparatus of claim 1, wherein the first pad has a first shape and the second pad has a second shape, the first shape being different than the second shape.

8. The apparatus of claim 1, wherein the first pad is has a first width and a first length, the second pad has a second width and a second length, the first width being larger than the second width, the first length being substantially the same as the second length.

9. The apparatus of claim 1, wherein at least a portion of the first pad includes an absorptive material and at least a portion of the second pad includes an absorptive material.

10. The apparatus of claim 1, wherein the base member is configured to be releasably coupled to an orthosis via a snap connection.

11. An apparatus, comprising:
an electrode base;
a first conductor member coupled to the electrode base;
a second conductor member coupled to the electrode base;
a first pad coupled to the electrode base such that the first conductor member is disposed between the electrode base and the first pad, a portion of the first pad configured to contact a skin surface; and
a second pad coupled to the electrode base such that the second conductor member is disposed between the electrode base and the second pad, a portion of the second pad configured to contact the skin surface; and
a panel member configured to be releasably coupled to an orthosis such that the first conductor member and the second conductor member are each electrically coupled to the orthosis and not electrically coupled to each other.

12. The apparatus of claim 11, wherein the first pad has a width between 30 mm and 75 mm and a length of about 95 mm, and the second pad has a width between 30 mm and 75 mm and a length of about 95 mm.

13. The apparatus of claim 11, wherein the first pad and second pad are each coupled to the electrode base such that there is a gap between the first pad and the second pad.

14. The apparatus of claim 11, wherein the first pad and second pad are each coupled to the electrode base such that there is a non-zero distance between the first pad and the second pad of between 1.5 mm and 2.5 mm.

15. The apparatus of claim 11, wherein the first pad has a substantially rectangular shape and the second pad has a substantially rectangular shape.

16. The apparatus of claim 11, wherein the first pad has a first shape and the second pad has a second shape, the first shape being different than the second shape.

17. The apparatus of claim 11, wherein the first pad is has a first width and a first length, the second pad has a second width and a second length, the first width being larger than the second width, the first length being substantially the same as the second length.

* * * * *

UNITED STATES PATENT AND TRADEMARK OFFICE
CERTIFICATE OF CORRECTION

PATENT NO.       : 8,868,217 B2  
APPLICATION NO.  : 13/169553  
DATED            : October 21, 2014  
INVENTOR(S)      : Dar et al.

Page 1 of 1

It is certified that error appears in the above-identified patent and that said Letters Patent is hereby corrected as shown below:

In the Specification

Column 8, line 39: delete "second o member" and insert --second member--;
Column 9, line 48: delete "of the electrode carrier";
Column 9, line 49: delete "magnetic" and insert --a magnetic--;
Column 9, line 58: delete "and" and insert --an--.

Signed and Sealed this
Twenty-sixth Day of May, 2015

Michelle K. Lee
*Director of the United States Patent and Trademark Office*